US011197908B2

(12) United States Patent
Servoss et al.

(10) Patent No.: US 11,197,908 B2
(45) Date of Patent: Dec. 14, 2021

(54) PEPTOIDS AND METHODS FOR ATTENUATING INFLAMMATORY RESPONSE

(71) Applicants: THE BOARD OF TRUSTEES OF THE UNIVERSITY OF ARKANSAS, Little Rock, AR (US); UNIVERSITY OF SOUTH CAROLINA, Columbia, SC (US)

(72) Inventors: Shannon Servoss, Fayetteville, AR (US); Melissa Moss, Columbia, SC (US); Lauren Wolf, Columbia, SC (US)

(73) Assignees: The Board of Trustees of the University of Arkansas, Little Rock, AR (US); University of South Carolina, Columbia, SC (US)

( * ) Notice: Subject to any disclaimer, the term of this patent is extended or adjusted under 35 U.S.C. 154(b) by 172 days.

(21) Appl. No.: 16/514,107

(22) Filed: Jul. 17, 2019

(65) Prior Publication Data

US 2020/0023032 A1 Jan. 23, 2020

Related U.S. Application Data

(60) Provisional application No. 62/699,296, filed on Jul. 17, 2018.

(51) Int. Cl.
*A61K 38/08* (2019.01)

(52) U.S. Cl.
CPC .................... *A61K 38/08* (2013.01)

(58) Field of Classification Search
CPC ...................................... A61K 38/08
See application file for complete search history.

(56) References Cited

U.S. PATENT DOCUMENTS

| 6,787,319 | B2 | 9/2004 | Ozenberger |
| 8,445,632 | B2 | 5/2013 | Barron et al. |
| 8,809,275 | B2 | 8/2014 | Servoss |
| 2012/0237552 | A1 | 9/2012 | Moreno |
| 2016/0376311 | A1 | 12/2016 | Servoss |

FOREIGN PATENT DOCUMENTS

| CN | 101357893 A | 2/2009 |
| CN | 105753940 A | 7/2016 |
| KR | 20140093596 A | 4/2017 |
| WO | 2009136382 A2 | 11/2009 |
| WO | 2011156003 | 12/2011 |
| WO | 2015005443 A1 | 1/2015 |
| WO | 2015177367 A1 | 11/2015 |
| WO | 2016158810 A1 | 10/2016 |
| WO | 2017127528 A1 | 7/2017 |
| WO | 2018026441 A1 | 2/2018 |

OTHER PUBLICATIONS

Mojsoska et al., "Structure-Activity Relationship Study of Novel Peptoids That Mimic the Structure of Antimicrobial Peptides," Antimicrobial Agents and Chemmotherapy, 2015, 59(7): 4112-4120. (Year: 2015).*
Watanabe, K., et al. Inhibitors of Fibril Formation and Cytotoxicity of Beta-Amyloid Peptide Composed of KLVFF Recognition Element and Flexible Hydrophilic Disrupting Element. Biochem. Biophys. Res. Commun. 2002, 290, 121-124.
Watson, J. "The Amyloid Beta face of Alzheimer's Disease," accessed from Anti-Agingfirewalls.com 2014.
Wetzels S, et al. Methylglyoxal-DerivedAdvanced Glycation Endproducts in Multiple Sclerosis. Int J Mol Sci. 2017;18(2):421.
Wolf LM, et al. Peptoids : Emerging Therapeutics for Neurodegeneration. 2017;2:1-5.
Wolf, L. M., et al. "Peptoid JPT1A Reduces Rage Expression and Attenuates Inflammatory Response: A Potential AD Therapeutic." Biophysical Journal 114.3 (2018): 465a.
Wu, C. W., et al. Peptoid Oligomers with Alpha-Chiral, Aromatic Side Chains: Effects of Chain Length on Secondary Structure. J. Am. Chem. Soc. 2001, 123, 2958-2963.
Wu, C. W., et al. Peptoid Oligomers with Alpha-Chiral, Aromatic Side Chains: Sequence Requirements for the Formation of Stable Peptoid Helices. J Am. Chem. Soc 2001, 123, 6778-6784.
Wu, J. W., et al. Fibrillar Oligomers Nucleate the Oligomerization of Monomeric Amyloid??? But Do Not Seed Fibril Formation. J. Biol. Chem. 2010, 285, 6071-6079.
Wu, W., et al. Fibrillar Seeds Alleviate Amyloid-? Cytotoxicity by Omitting Formation of Higher-Molecular-Weight Oligomers. Biochem. Biophys. Res. Commun. 2013, 439, 321-326.
Zuckermann, R.N. et al., "Efficient method for the preparation of peptoids [Oligo(N-substituted glycines)] by submonomer solid-phase synthesis," (1992) J. Am. Chem. Soc. 114:10646-10647.
Adessi, C. et al., "Pharmacological profiles of peptide drug candidates for the treatment of Alzheimer's disease," (2003) J. Biological Chemistry 278(16):13905-13911.
Aileen Funke, S.; et al. Peptides for Therapy and Diagnosis of Alzheimer's Disease. Curr Pharm. Des. 2012, 18, 755-767.
Burstein AH, et al. Effect of TTP488 in patients with mild to moderate Alzheimer's disease. BMC Neurol. 2014;14:12.
Byun K, et al. Advanced glycation end-products produced systemically and by macrophages: A common contributor to inflammation and degenerative diseases. Pharmacol Ther. 2017.
Chan, C., et al. "Peptoid inhibition of trypanothione reductase as a potential antitrypanosomal and antileishmanial drug lead." Amino acids 22.4 (2002): 297-308.
Churches, Q. I., et al. Naturally Occurring Polyphenolic Inhibitors of Amyloid Beta Aggregation. Bioorganic Med. Chem. Lett. 2014, 24, 3108-3112.
Esler, W. P., et al. Point Substitution in the Central Hydrophobic Cluster of a Human Beta-Amyloid Congener Disrupts Peptide Folding and Abolishes Plaque Competence. Biochemistry 1996, 35, 13914-13921.

(Continued)

*Primary Examiner* — Julie Ha
(74) *Attorney, Agent, or Firm* — Quarles & Brady LLP

(57) ABSTRACT

Disclosed herein are peptoids and methods for attenuating inflammatory responses, and more particularly RAGE-associated inflammatory responses.

17 Claims, 13 Drawing Sheets

(56) References Cited

OTHER PUBLICATIONS

Etienne, M. A., et al. Beta-Amyloid Protein Aggregation. Methods Mol. Biol. Clift. NJ 2007, 386, 203-225.

Franklin TC, et al. Persistent increase in microglial RAGE contributes to chronic stress Induced priming of depressive-like behavior. Biol Psychiatry. 2017.

Friguei B, et al. Measurements of the true affinity constant in solution of antigen-antibody complexes by enzyme-linked immunosorbent assay. J Immunol Methods. 1985;77(2):305-319.

Galasko D, et al. Clinical trial of an inhibitor of RAGE-Aß interactions in Alzheimer disease. Neurology. 2014;82(17):1536-1542.

Goldsbury, C., et al. a. Multiple Assembly Pathways Underlie Amyloid-? Fibril Polymorphisms. J. Mol. Biol. 2005, 352, 282-298.

Hamley, I. W., et al. Alignment of a Model Amyloid Peptide Fragment in Bulk and at a Solid Surface. J. Phys. Chem. B 2010, 114, 8244-8254.

Hara, T., et al. "Probing the structural requirements of peptoids that inhibit hDM2-p53 interactions." Journal of the American Chemical Society 128.6 (2006): 1995-2004.

Hardy, J., et al. The Amyloid Hypothesis of Alzheimer's Disease: Progress and Problems on the Road to Therapeutics. Science 2002, 297, 353-356.

Herrera J., "Peptoid-based therapeutics for Alzheimer's disease," Abstract presented at American Institute of Chemical Engineers 2009 Annual Meeting, Monday, Nov. 9, 2009.

Hudson, S., et al. The Thioflavin T Fluorescence Assay for Amyloid Fibril Detection Can Be Biased by the Presence of Exogenous Compounds FEBS J. 2009, 276, 5960-5972.

Juranek JK, et al. Receptor for Advanced Glycation End Products and its Inflammatory Ligands are Upregulated in Amyotrophic Lateral Sclerosis. Front Cell Neurosci. 2015;9(December):485.

Kierdorf K, et al. RAGE regulation and signaling in inflammation and beyond. J Leukoc Biol. 2013;94(July):55-68.

Kirshenbaum, K., et al. Sequence-Specific Polypeptoids: A Diverse Family of Heteropolymers with Stable Secondary Structure. Proc. Natl. Acad. Sci. U. S. A. 1998, 95, 4303-4308.

Koborova I, et al. Association between metabolically healthy central obesity in women and levels of soluble receptol for advanced glycation end products, soluble vascular adhesion protein-1, and the activity of semicarbazide-sensitive amine oxidase. Croat Med J. 2017;58(2):106-116.

Kuperstein, I. et al., "Neurotoxicity of Alzheimer's disease Aß peptides is induced by small changes in the Aß42 to Aß40 ratio," EMBO Journal 2010, 29:3408-3420.

Laursen, J. S., et al. Cis-Trans Amide Bond Rotamers in???-Peptoids and Peptoids: Evaluation of Stereoelectronic Effects in Backbone and Side Chains. J. Am. Chem. Soc. 2013, 135, 2835-2844.

Lee, S. et al, Small heat shock proteins differentially affect Aß aggregation and toxicity. Biochem Biophys Res Comm, 2006, vol. 347, 527-533.

Lowe, T. L., et al. Structure-Function Relationships for Inhibitors of Beta-Amyloid Toxicity Containing the Recognition Sequence KLVFF. Biochemistry 2001, 40, 7882-7889.

Luo, Y. et al. Inhibiting and reversing amyloid-b peptide 140 fibril formation with gramicidin S and engineered analogues. Chem Eur J. 2013. 19:17338-17348.

Luo, Y., et al. Aß42-Binding Peptides as Amyloid Aggregation Inhibitors and Detection Ligands. ACS Chemical Neuroscience. 2013. vol. 4. 952-962.

Miller, S. M., et al. Comparison of the Proteolytic Susceptibilities of Homologous L-Amino Acid, D-Amino Acid, and N-Substituted Glycine Peptide and Peptoid Oligomers. Drug Dev. Res. 1995, 35, 20-32.

Moss, M.A et al., "The peptide KLVFF-K(6) promotes beta-amyloid(1-40) protofibril growth by association but does not alter protofibril effects on cellular reduction of 3-(4,5-dimethylthiazol-2-yl)-2,5-diphenyltetrazolium bromide (MTT)," (2003) Mol. Pharmacol. (5):1160-1168.

Nilsson, M. R. Techniques to Study Amyloid Fibril Formation in Vitro. Methods 2004, 34, 151-160.

Office action for U.S. Appl. No. 13/656,198 dated Dec. 27, 2013.

Patch et al., "Versatile Oligo(N-substituted) glycines: The many roles of peptoids in drug discovery;" Pseudo-Peptides in Drug Discovery; Wiley-VCG Verlag (2004).

Patel, D. et al. Attenuation of ß-amyloid induced toxicity by sialic acid-conjugated dendrimeric polymers. 2006. Biochimica et Biophysica Acta (BBA). vol. 1760:12. 1802-1809.

Pike, C. J., et al. Amino-Terminal Deletions Enhance Aggregation of beta-Amyloid Peptides in Vitro. 1995.

Raffi and Aisen, Recent Developments in Alzheimer's Disease Therapeutics. BMC Medicine. 2009. 7:7.

Rajasekhar, K., et al. Rationally Designed Peptidomimetic Modulators of Aß Toxicity in Alzheimer's Disease. Sci. Rep. 2015, 5, 8139.

Rosenman, D. J., et al. Aß Monomers Transiently Sample Oligomer and Fibril-like Configurations: Ensemble Characterization Using a Combined MD/NMR Approach. J. Mol. Biol. 2013, 425, 3338-3359.

Sanborn, T. J., et al. Extreme Stability of Helices Formed by Water-Soluble Poly-N-Substituted Glycines (polypeptoids) with Alpha-Chiral Side Chains. Biopolymers 2002, 63, 12-20.

Sengupta, U. et al. "The Role of Amyloid-ß Oligomers in Toxicity, Propagation, and Immunotherapy," EBioMedicine 2016, 6:42-49.

Soto-Ortega, D.D. et al., "Inhibition of amyloid-ß aggregation by coumarin analogs can be manipulated by functionalization of the aromatic center," (2011) Bioorganic & Medicinal Chem. 19:2596-2602.

Sparvero LJ, et al. RAGE (Receptor for Advanced Glycation Endproducts), RAGE ligands, and their role in cancer and inflammation. J Transl Med. 2009;7:17.

Sturchler E, et al. Site-Specific Blockade of RAGE-V d Prevents Amyloid-Oligomer Neurotoxicity. Neuroscience. 2008;28(20):5149-5158.

Tamada, K., et al. "Papaverine identified as an inhibitor of high mobility group box 1/receptor for advanced glycation end-products interaction suppresses high mobility group box 1-mediated inflammatory responses." Biochemical and biophysical research communications 511.3 (2019): 665-670.

Teplow, D. B. Preparation of Amyloid Beta-Protein for Structural and Functional Studies. Methods Enzymol. 2006, 413, 20-33.

Tjernberg, L. O., et al. Arrest of Beta-Amyloid Fibril Formation by a Pentapeptide Ligand. J. Biol. Chem. 1996, 271, 8545-8548.

Tjernberg, L. O., et al. Controlling Amyloid Beta-Peptide Fibril Formation with Protease-Stable Ligands. J. Biol. Chem. 1997, 272, 12601-12605.

Tran, T-A, et al. "Design, synthesis, and biological activities of potent and selective somatostatin analogues incorporating novel peptoid residues." Journal of medicinal chemistry 41.15 (1998): 2679-2685.

Turner JP, et al. Modulating amyloid-ß aggregation: The effects of peptoid side chain placement and chirality. Bioorg Med Chem. 2017;1(1):1-7.

Turner JP, et al. Rationally Designed Peptoids Modulate Aggregation of Amyloid-Beta 40. ACS Chem. Neurosci. 2014.

Turner JP, et al., "Peptoids: A potential therapeutic agent against Alzheimer's disease," Abstract presented at American Institute of Chemical Engineers 2011 Annual Meeting, Wednesday, Oct. 19, 2011 (Available online Oct. 13, 2011).

* cited by examiner

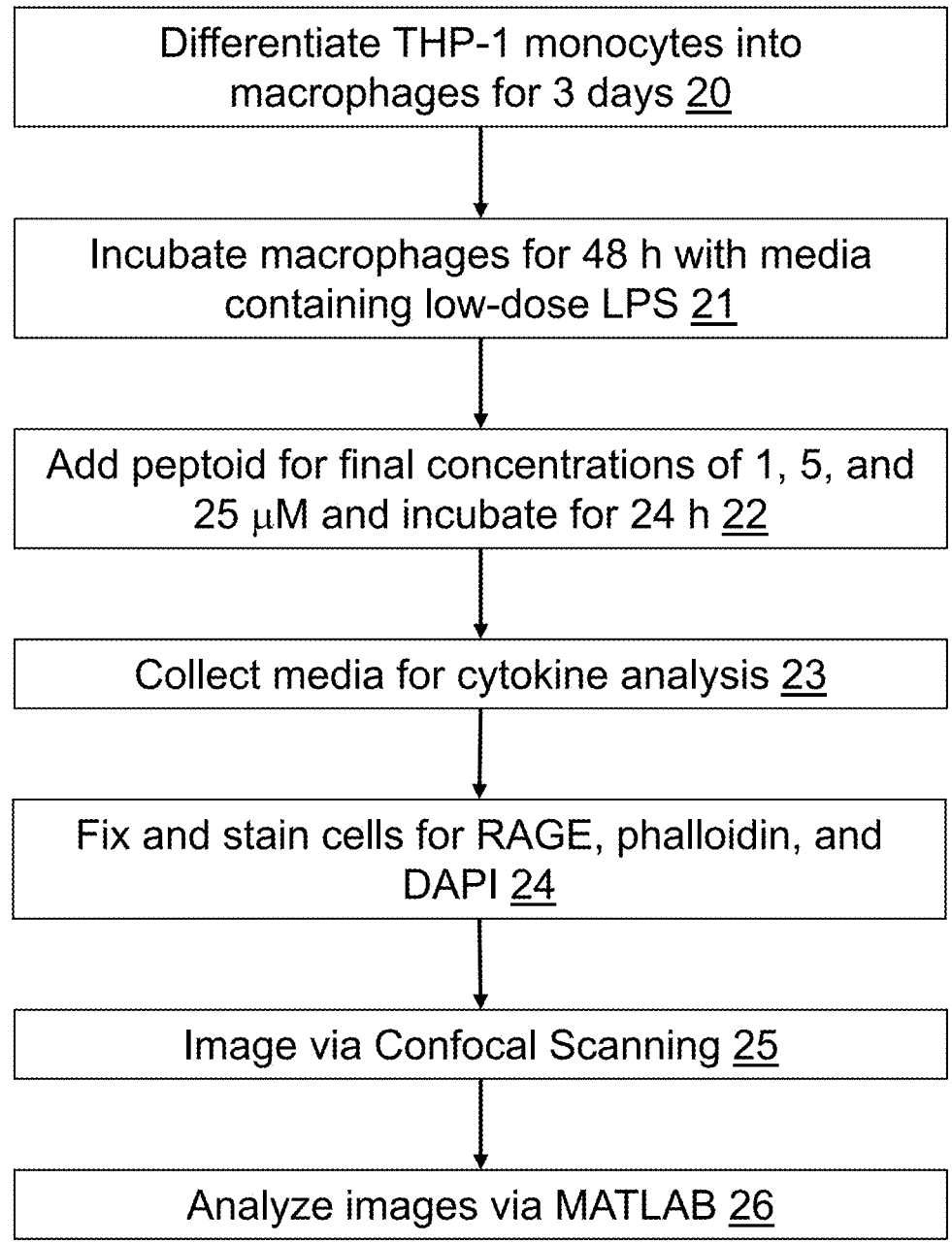

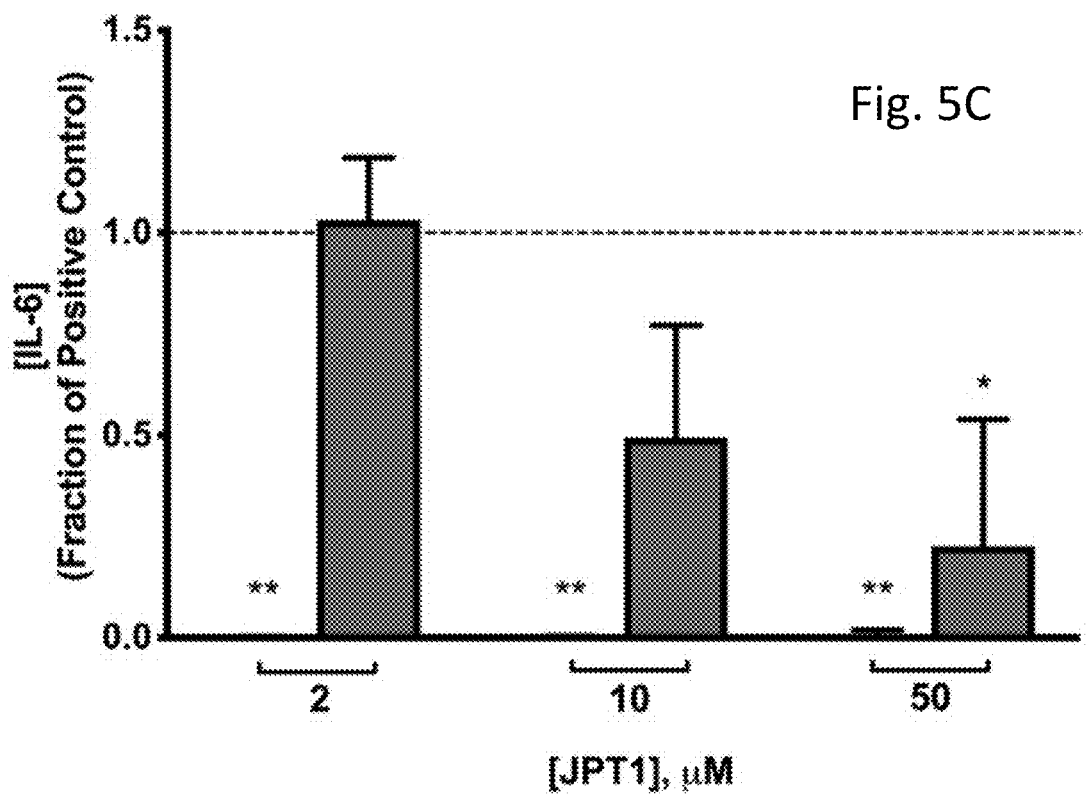
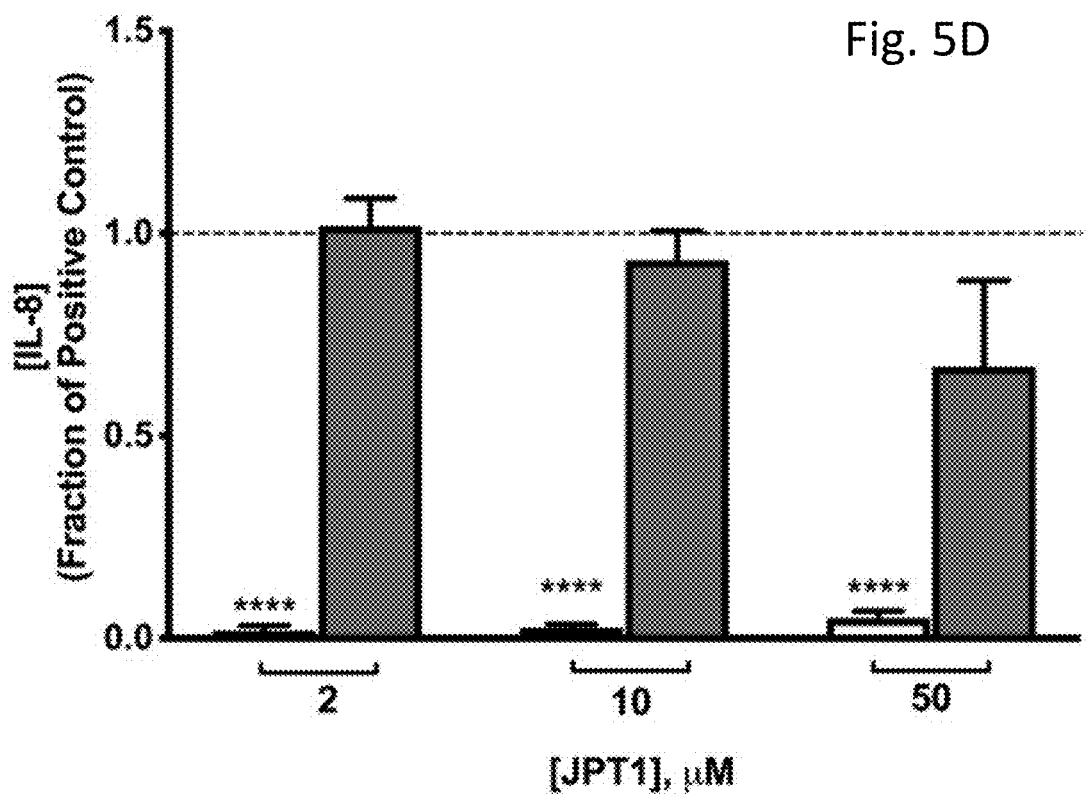

PEPTOIDS AND METHODS FOR ATTENUATING INFLAMMATORY RESPONSE

CROSS-REFERENCE TO RELATED APPLICATIONS

This patent application claims the benefit of priority of U.S. Provisional Patent Application No. 62/699,296, filed on Jul. 17, 2018, which is incorporated herein by reference in its entirety.

BACKGROUND

Peptoids are peptidomimetics that attain invulnerability to proteolytic degradation through repositioning of the side-chain from the α-carbon to the amide nitrogen. This invulnerability to proteases, as well as other qualities such as diminished immunogenicity, enhanced cellular permeability, and capacity for intranasal administration, make peptoids immensely attractive as neurotherapeutic agents.

A peptoid mimic of Aβ's KLVFF hydrophobic core, JPT1a, has the capacity to modulate $A\beta_{1-40}$ aggregation as well as alter the morphology of $A\beta_{1-40}$ aggregates [US Pub. No. 2016/0376311, published Dec. 29, 2016 to Servoss et al.]. Amyloid-β (Aβ) has been the key therapeutic target for Alzheimer disease (AD)-related therapies, but more recent studies have recast Aβ as one of several participants in the disease rather than its sole etiology. Recent clinical trials have shown that targeting AD-associated inflammation using an antagonist for the receptor for advanced glycation end products (RAGE) improves outcomes in patients with mild-to-moderate AD. As a result, there is a need for compositions that target RAGE-associated inflammation or antagonize RAGE.

BRIEF SUMMARY OF THE INVENTION

Disclosed herein are peptoids and methods for attenuating inflammatory responses, and more particularly RAGE-associated inflammatory responses. Methods for reversing or inhibiting RAGE expression in a cell presented with a stimulator of an innate immune response are provided. The methods comprise contacting the cell with an effective amount of a composition comprising a peptoid segment of formula

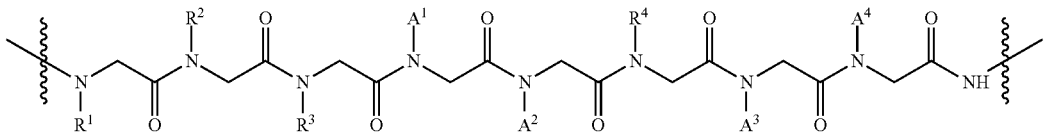

to reverse or inhibit RAGE expression in the cell. Each of $R^1$, $R^2$, $R^3$, and $R^4$ may be independently selected from a branched or an unbranched, saturated or unsaturated, substituted or unsubstituted $C_1$-$C_{10}$ alkyl group, and each of $A^1$, $A^2$, $A^3$, and $A^4$ may be independently selected from a branched or an unbranched, substituted or unsubstituted $C_6$-$C_{12}$ aryl or $C_6$-$C_{12}$ arylalkyl group. The stimulator of the innate immune response may be damage-associated molecular pattern (DAMP) or pathogen-associated molecular pattern (PAMP) molecules. Examples of stimulators include, without limitation, an advanced glycation endproduct (AGE), amyloid-β (Aβ), HMGB1, a S100, a nucleic acid, a bacterial endotoxin, and a virus.

The methods may also allow for accumulation of a cytokine in the cell or production of a cytokine by the cell to be reversed or inhibited. Suitably, the cytokine comprises IL-1β, IL-6, IL-8, or a combination thereof.

Another aspect of the invention is a method for slowing or reversing progression of a RAGE-associated disease or disorder in a subject suffering therefrom. The method may comprise administering a therapeutically effective amount of a composition comprising a peptoid segment of formula

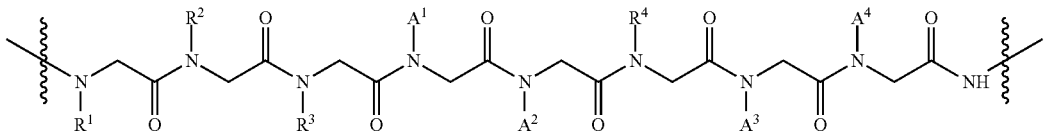

to the subject to slow or reverse progression of the RAGE-associated disease or disorder. Each of $R^1$, $R^2$, $R^3$, and $R^4$ may be independently selected from a branched or an unbranched, saturated or unsaturated, substituted or unsubstituted $C_1$-$C_{10}$ alkyl group, and each of $A^1$, $A^2$, $A^3$, and $A^4$ may be independently selected from a branched or an unbranched, substituted or unsubstituted $C_6$-$C_{12}$ aryl or $C_6$-$C_{12}$ arylalkyl group. The composition may be a pharmaceutical composition comprising the peptoid and a pharmaceutically acceptable carrier. The RAGE-associated disease or disorder may be Alzheimer's disease, arthritis, rheumatoid arthritis, Takayasu's arthritis, atherosclerosis, congestive heart failure, myocardial infarction, peripheral vascular disease, diabetic neuropathy, diabetic nephropathy, diabetic retinopathy, psoriasis, Parkinson's disease, multiple sclerosis, amyotrophic lateral sclerosis, or Creutzfeldt-Jakob disease.

With either of the methods described above, the peptoid may comprise a longer peptoid chain than the segment. In other embodiments, the peptoid comprises

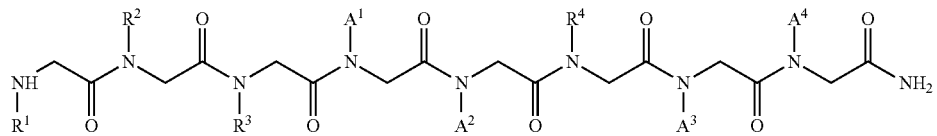

Suitably, $R^1$ may comprise a terminally substituted $C_1$-$C_6$ aminoalkyl group. In certain embodiments, $R^1$ comprises 4-butylamine. Suitably, $R^2$, $R^3$, and $R^4$ may be independently selected from a branched or an unbranched, saturated or unsaturated, substituted or unsubstituted $C_1$-$C_6$ alkyl group. In some embodiments, each of $R^2$, $R^3$, and $R^4$ comprise the same group. Suitably, $A^1$, $A^2$, $A^3$, and $A^4$ may be independently selected from a branched or an unbranched, substituted or unsubstituted $C_6$-$C_{12}$ aryl or $C_6$-$C_{12}$ arylalkyl group.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIG. 3 provides a schematic representation for evaluating reversal of RAGE.

FIGS. 5B-5D show that JPT1 attenuates pro-inflammatory cytokine expression of IL-1β (FIG. 5B), IL-6 (FIG. 5C), and IL-8 (FIG. 5D).

FIGS. 7A-7B show the concentration of bound RAGE as a function of RAGE concentration (FIG. 7A) and E-cadherin concentration (FIG. 7B). FIGS. 7C-7D show Scatchard plots for JPT1a (FIG. 7C) and JPT1 (FIG. 7D).

FIG. 9 demonstrates reduction in $A\beta_{1\text{-}42}$ oligomer induced RAGE expression in macrophages treated with JPT1a.

DETAILED DESCRIPTION OF THE INVENTION

Figure 1:
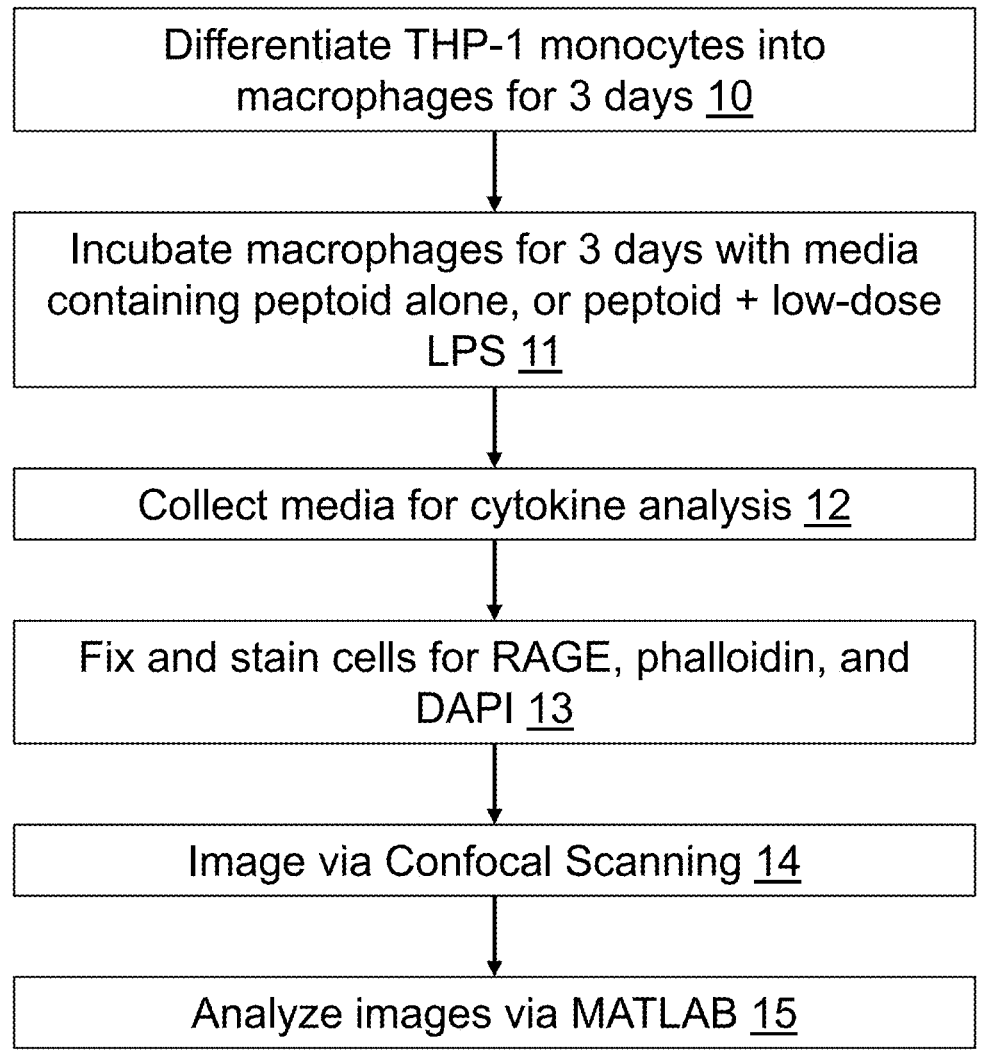
FIG. 1 provides a schematic illustration for evaluating upregulation of RAGE and modulation of inflammatory response.

Disclosed herein are peptoids and methods for attenuating inflammatory responses, and more particularly RAGE-associated inflammatory responses. As demonstrated in the Examples that follow, co-incubation of a peptoid, such as JPT1a or JPT1, with the pro-inflammatory stimulus LPS significantly reduces RAGE upregulation in a dose dependent manner within a chronic inflammation model that utilizes THP-1 macrophages. In parallel, the peptoids disclosed herein also reduce the production of pro-inflammatory cytokines IL-1β, IL-6, and IL-8. When paralleled by the ability of these peptoids to reverse RAGE expression, these results demonstrate the potential of peptoids, such as JPT1a or JPT1, as a dual-target therapy in AD, modulating both inflammation and Aβ aggregation. Moreover, RAGE is a promising therapeutic target in several pathologies, so a RAGE inhibitor, such as the peptoids described herein, yields new therapeutic options to a wide array of illnesses.

RAGE is a 35 kDa transmembrane receptor of the immunoglobulin super family and is implicated in diverse chronic inflammatory states. RAGE's name comes from its ability to bind advanced glycation end-products (AGE), which include glycoproteins, but RAGE is a multi-ligand pattern recognition receptor that binds and mediates the cellular response to a range of damage-associated molecular pattern molecules (DAMPs) including AGEs, Aβ, HMGB1, S100s, CD11b, RNA, and DNA. Additional RAGE ligands include, glycosylated sugars, heparan sulfate, high mobility group box 1 (HMGB1), lysophosphatidic acid (LPA), lipopolysaccharide (LPS), Mac-1, methylglyoxal-derived hydroimidazolone (MG-H1), phosphatidylserine, prions (i.e. prion diseases), quinolinic acid, and transthyretin. RAGE can also act as an innate immune sensor of microbial pathogen-associated molecular pattern molecules (PAMPs) including bacterial endotoxin, respiratory viruses, and microbial DNA. RAGE is expressed at low levels under normal physiology, but it is highly upregulated under chronic inflammation because of the accumulation of various RAGE ligands.

The interaction between RAGE and its ligands is believed to result in pro-inflammatory gene activation. Ligand binding results in RAGE signal activation of nuclear factor kappa B (NF-κB), and RAGE, itself, is upregulated by NF-κB. Due to an enhanced level of RAGE ligands in many chronic diseases and cancers, a positive feedback cycle can be established. Therefore, RAGE is believed to have a causative effect with inflammatory diseases, including, without limitation, Alzheimer's disease, arthritis, rheumatoid arthritis, Takayasu's arthritis, atherosclerosis, congestive heart failure, myocardial infarction, peripheral vascular disease, diabetic neuropathy, diabetic nephropathy, diabetic retinopathy, psoriasis, Parkinson's disease, multiple sclerosis, amyotrophic lateral sclerosis, or Creutzfeldt-Jakob disease.

Peptoids are a class of peptidomimetics that are ideal candidates for use as therapeutic and detection agents due to their increased bioavailability (i.e. resistance to protease degradation) and low immune response. Peptoids have a backbone similar to peptides with the side chains attached to the amide nitrogen rather than the alpha-carbon. This small backbone change imparts protease resistance as well as an achiral backbone. However, inclusion of chiral side chains within the peptoid sequence allows for the formation of helical secondary structures. Specifically, peptoids containing chiral, aromatic side chains adopt a polyproline type-I like helix, which exhibits a ~6 Å helical pitch and 3 monomers per turn. Peptoid helices are extremely stable and do not denature in up to 8 M urea with temperatures up to 70° C. Peptoids allow for greater bioavailability than peptides since peptoid monomers are linked with an imide bond, which is resistant to proteolytic degradation, and the absence of hydrogen in amide groups in the backbone of the peptoids reduces compound polarity and improves membrane permeability. Use of peptoids may also reduce toxicity associated with peptide breakdown products. The peptoids described herein may be made and used using methods available to those skilled in the art. For example, see Zuckermann et al. Current Opinion in Molecular Therapeutics 11:299-307 (2009) and Ovadia et al. Bioorganic & Medicinal Chemistry 18:580-589 (2010) for information pertaining to the preparation and use of peptoids as therapeutics, the entire contents of which are incorporated herein in their entireties.

The peptoid disclosed herein is designed to attenuate a RAGE-associated inflammatory response. The peptoid may comprise a segment of a longer peptoid chain having the following general formula

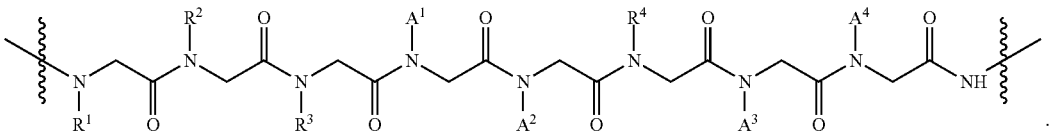

As used herein, a monomer of the peptoid is a single (—NX—CH$_2$—CO—) group, where X is a side chain. Suitably, the peptoids are achiral or all the monomers have the same chirality. The peptoids shown may also be part of a larger peptoid. Such larger peptoids may include more than 8 monomers. For example the peptoid may comprise 10, 12, 15, 18, 20, 25, 30, 35 or any number of monomers therebetween. The additional monomers may be included on either end of the active peptoids described herein or may be included on only a single end.

In certain embodiments, the peptoid comprises an eight monomer peptoid having the general formula:

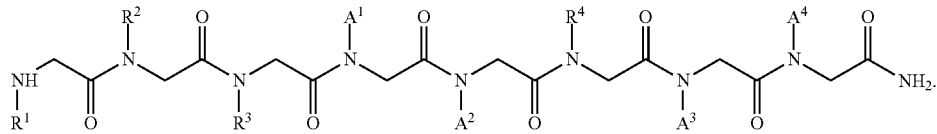

In some embodiments, the peptoid comprising eight residues is achiral.

In either of the formulas above, the R side chains of the peptoid are branched or unbranched, saturated or unsaturated, substituted or unsubstituted $C_1$-$C_{10}$ alkyl groups, and the A side chains of the peptoid comprise branched or an unbranched, substituted or unsubstituted $C_6$-$C_{12}$ aryl or $C_6$-$C_{12}$ arylalkyl groups.

$R^1$ may be selected from an unbranched, substituted or unsubstituted $C_1$-$C_{10}$, including without limitation a $C_1$-$C_6$ alkyl or a $C_2$-$C_5$ alkyl. If $R^1$ is substituted, the substitution is suitably a substituent comprising nitrogen such as an amine. $R^1$ may comprise a terminally substituted $C_1$-$C_{10}$ aminoalkyl group, including without limitation a terminally substituted $C_1$-$C_6$ aminoalkyl group or a terminally substituted $C_2$-$C_5$ aminoalkyl group. $R^1$ may have a positive charge or may be neutral. With the peptoid employed with the Examples, $R^1$ is 4-aminobutyl and the first monomer is N-(4-aminobutyl)glycine.

Each of $R^2$, $R^3$, and $R^4$ may independently be selected as an unsubstituted $C_1$-$C_{10}$ alkyl group, including without limitation an unsubstituted $C_1$-$C_6$ alkyl group or an unsubstituted $C_2$-$C_5$ alkyl group. In some embodiments, each of $R^2$, $R^3$, and $R^4$ comprise the same group. With the peptoid employed in the Examples, each of $R^2$, $R^3$, and $R^4$ may independently comprise a propyl group or a 1-methyl-prop-1-yl group.

Each of $A^1$, $A^2$, $A^3$, and $A^4$ may be independently selected from an unsubstituted $C_6$-$C_{12}$ aryl or $C_6$-$C_{12}$ arylalkyl group, including without limitation a $C_6$ aryl, a $C_7$-$C_{10}$ arylalkyl, or a $C_7$-$C_8$ aryl alkyl. In some embodiments, each of $A^1$, $A^2$, $A^3$, and $A^4$ comprise the same group. In some embodiments, each of $A^1$, $A^2$, $A^3$, and $A^4$ may independently comprise a benzyl group or a 1-phenylethyl group. With the peptoid employed in the Examples, each of $A^1$, $A^2$, $A^3$, and $A^4$ comprise a —$CH_2C_6H_5$ group or —$CH(CH_3)C_6H_5$.

In some embodiments, the R and A groups are unbranched. In other embodiments the R and A groups are branched.

Table 1 shows the structure of exemplary peptoids JPT1a and JPT1, which may be made according to US Pat. Pub. 2016/0376311 and are used in the Examples. The Examples demonstrate that JPT1a is capable of reducing RAGE upregulation in a dose dependent manner and reduces the production of pro-inflammatory cytokines. The structure of JPT1a is shown in Table 1 and includes in the context of the general formulas above, $R^1$ of —$(CH_2)_3NH_3^+$; $R^2$, $R^3$, and $R^4$ of —$(CH_2)_2CH_3$; and $A^1$, $A^2$, $A^3$, and $A^4$ is $CH_2C_6H_5$. The alkyl portion of each side chain (R or A side chains) may have a variable length, and the resulting peptoid is expected to attenuate RAGE-associated inflammatory responses.

aryl or arylalkyl. In other embodiments, one third or up to two thirds of the monomers have aryl or arylalkyl groups such that one or two out of every three side groups in the peptoid are aryl or arylalkyl groups. Suitably, the aryl or aryl alkyl groups are —$CH_2C_6H_5$ or —$CH(CH_3)C_6H_5$ as shown in Table 1. Suitably, additional aryl or arylalkyl groups may be used such as a phenyl, phenylethyl, phenylpropyl, or phenylbutyl. The aryl portion of the groups may include between 6 and 30 carbons. The arylalkyl may be unbranched, substituted, or unsubstituted, and the alkyl portion may be saturated or unsaturated. Suitably, the aryl or arylalkyl groups are unsubstituted or substituted with N, S, or O.

The remaining side chains may be branched or unbranched, substituted or unsubstituted, saturated or unsaturated $C_1$-$C_{10}$ alkyl or $C_4$-$C_{10}$ cycloalkyl groups, such as those shown as R in the generic formula above. The R group is suitably a branched or unbranched, substituted or

TABLE 1

Structure and molecular weight of peptoids used herein.

| Name | Structure | MW (Da) |
|---|---|---|
| JPT1a | 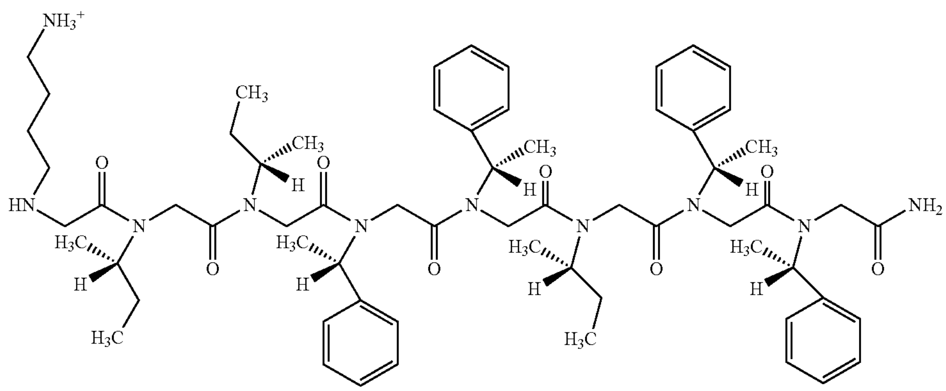 [SMILES: CC[C@H](C)N(CC(=O)N(CC(=O)N(CC(=O)N(CC(=O)N(CC(=O)N(CC(=O)N(CC(N)=O)[C@@H](C)c1ccccc1)[C@@H](C)c1ccccc1)[C@@H](C)CC)[C@@H](C)c1ccccc1)[C@@H](C)c1ccccc1)[C@@H](C)CC)C(=O)CNCCCC[NH3+]] | 1032 |
| JPT1 | 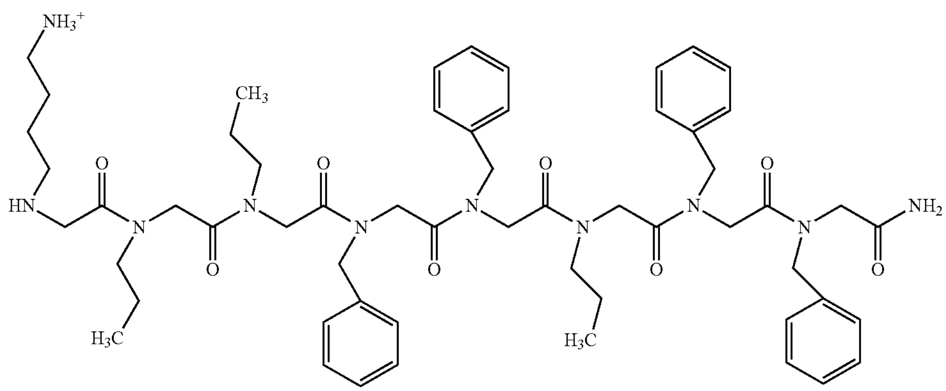 [SMILES: CCCN(CC(=O)N(CCC)CC(=O)N(CC(=O)N(CC(=O)N(CCC)CC(=O)N(CC(=O)N(CC(N)=O)Cc1ccccc1)Cc1ccccc1)Cc1ccccc1)Cc1ccccc1)C(=O)CNCCCC[NH3+]] | 1130 |

In the peptoids described herein, at least two and as many as two-thirds of the monomers have side groups that are aryl or arylalkyl groups, such as those shown as A in the generic formula above. Suitably, the aryl or arylalkyl groups are arranged in the peptoid such that the peptoid has aryl or arylalkyl groups that are separated by two monomers. The peptoids may form a helical structure with three monomers per helical turn of the peptoid such that the aryl or arylalkyl groups are stacked on one side of the helix in the peptoids. In some embodiments, the aryl or arylalkyl groups are spaced such that every third monomer in the peptoid is an unsubstituted, saturated or unsaturated, $C_1$-$C_{10}$ alky, $C_4$-$C_{10}$ aryl, $C_4$-$C_{10}$ arylalkyl, or $C_4$-$C_{10}$ cycloalkyl group. The R groups are independently selected from unbranched, substituted or unsubstituted, saturated or unsaturated, $C_1$-$C_{10}$ alkyl, aryl, heteroaryl, arylalkyl, cyclic, or heterocyclic groups. Suitably, the peptoid has at least eight monomers, similar to those shown in Table 1, in which $R^1$, $R^2$, $R^3$, and $R^4$ are independently selected from 4-aminobutyl, 3-aminopropyl, 2-aminoethyl, or aminomethyl, pentyl, butyl, propyl, ethyl, methyl. The R groups may be chiral or achiral as well.

The peptoids disclosed herein are capable of reversing or inhibiting RAGE expression in a cell presented with a stimulator of an innate immune response. Suitably, the peptoids are capable of reversing or inhibiting RAGE expression by at least 50% in a cell presented with a stimulator of the innate immune response, including without limitation by at least 60%, 70%, 75%, 80%, 85%, 90%, 93%, 95%, 97%, 98%, 99%, or more. Examples of stimulators of the innate immune response include DAMPs, e.g., AGEs, Aβ, HMGB1, S100s, and DNA, and PAMPs, e.g., bacterial endotoxin, viruses, and microbial DNA. As the Examples demonstrate, the peptoids disclosed herein are capable or reversing or inhibiting RAGE expression when macrophages are presented with the PAMP LPS and the DAMP Aβ.

The peptoids disclosed herein may also be capable of reversing or inhibiting cytokine accumulation in a cell presented with a stimulator of the innate immune response. Suitably, the peptoids are capable of reversing or inhibiting cytokine accumulation by at least 50% in a cell presented with a stimulator of the innate immune response, including without limitation by at least 60%, 70%, 75%, 80%, 85%, 90%, 93%, 95%, 97%, 98%, 99%, or more. The Examples also demonstrate the peptoids are capable of inhibiting the accumulation of pro-inflammatory cytokines, such as IL-1β, IL-6, and IL-8, when macrophages are presented with the PAMP LPS.

The term "alkyl group" is intended to mean a group of atoms derived from an alkane by the removal of one hydrogen atom. Thus, the term includes straight or branched chain alkyl moieties including, for example, methyl, ethyl, propyl, isopropyl, butyl, tert-butyl, pentyl, hexyl, and the like. Preferred alkyl groups contain from 1 to about 14 carbon atoms ($C_{1-14}$ alkyl).

The term "aryl group" is intended to mean a group derived from an aromatic hydrocarbon by removal of a hydrogen from the aromatic system. Preferred aryl groups contain phenyl or substituted phenyl groups. Thus, the term "aryl" includes an aromatic carbocyclic radical having a single ring or two condensed rings. This term includes, for example, phenyl or naphthyl.

The term "heteroaryl" refers to aromatic ring systems of five or more atoms (e.g., five to ten atoms) of which at least one atom is selected from O, N, and S and includes, for example, furanyl, thiophenyl, pyridyl, indolyl, quinolyl, and the like.

"Substituted" means that one or more of the hydrogen atoms bonded to carbon atoms in the chain or ring have been replaced with other substituents. Suitable substituents include monovalent hydrocarbon groups including alkyl groups such as methyl groups and monovalent heterogeneous groups including alkoxy groups such as methoxy groups or amines. "Unsubstituted" means that the carbon chain or ring contains no other substituents other than carbon and hydrogen.

"Branched" means that the carbon chain is not simply a linear chain. "Unbranched" means that the carbon chain is a linear carbon chain.

"Saturated" means that the carbon chain or ring does not contain any double or triple bonds. "Unsaturated" means that the carbon chain or ring contains at least one double bond. An unsaturated carbon chain or ring may include more than one double bond.

The term "acyl" or "acetyl group" is intended to mean a group having the formula RCO—, wherein R is an alkyl group or an aryl group.

The term "alkenyl" refers to a straight or branched chain alkyl moiety having two or more carbon atoms (e.g., two to six carbon atoms, $C_{2-6}$ alkenyl) and having in addition one double bond of either E or Z stereochemistry where applicable. This term would include, for example, vinyl, 1-propenyl, 1- and 2-butenyl, 2-methyl-2-propenyl, etc.

The term "cycloalkyl" refers to a saturated alicyclic moiety having three or more carbon atoms (e.g., from three to six carbon atoms) and which may be optionally benzofused at any available position. This term includes, for example, cyclopropyl, cyclobutyl, cyclopentyl, cyclohexyl, indanyl, and tetrahydronaphthyl.

The term "heterocycloalkyl" refers to a saturated heterocyclic moiety having three or more carbon atoms (e.g., from three to six carbon atoms) and one or more heteroatom from the group N, O, S (or oxidized versions thereof) and which may be optionally benzofused at any available position. This term includes, for example, azetidinyl, pyrrolidinyl, tetrahydrofuranyl, piperidinyl, indolinyl, and tetrahydroquinolinyl.

The term "cycloalkenyl" refers to an alicyclic moiety having three or more carbon atoms (e.g., from three to six carbon atoms) and having in addition one double bond. This term includes, for example, cyclopentenyl or cyclohexenyl.

The term "heterocycloalkenyl" refers to an alicyclic moiety having from three to six carbon atoms and one or more heteroatoms from the group N, O, S (or oxides thereof) and having in addition one double bond. This term includes, for example, dihydropyranyl.

The term "arylalkyl" refers to an alkyl group as defined above substituted with one or more aryl group as defined above. Suitably, the arylalkyl group is an alkyl group substituted with one aryl group such as a phenylethyl or phenylmethyl group.

The term "halogen" means a halogen of the periodic table, such as fluorine, chlorine, bromine, or iodine.

The term "optionally substituted" means optionally substituted with one or more of the aforementioned groups (e.g., alkyl, aryl, heteroaryl, acyl, alkenyl, cycloalkyl, heterocycloalkyl, cycloalkenyl, heterocycloalkenyl, nitrogen, oxygen, sulfur, or halogen) at any available position or positions.

The compounds may be synthesized using conventional chemical technologies available to those skilled in the art.

Salts of the compounds described herein are also provided. Suitably, the salts are pharmaceutically acceptable. Acceptable salts of the compounds include, but are not limited to, hydrochloride, hydrobromide, hydroiodide, nitrate, sulfate, bisulfate, phosphate, and acid phosphate.

The compounds may be used to make pharmaceutical compositions. Pharmaceutical compositions comprising the peptoids described above and a pharmaceutically acceptable carrier are provided. A pharmaceutically acceptable carrier is any carrier suitable for in vivo administration. Examples of pharmaceutically acceptable carriers suitable for use in the composition include, but are not limited to, water, buffered solutions, glucose solutions, and oil-based or bacterial culture fluids. Additional components of the compositions may suitably include, for example, excipients such as stabilizers, preservatives, diluents, emulsifiers, and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). Especially when such stabilizers are added to the compositions, the composition is suitable for freeze-drying or spray-drying. The composition may also be emulsified.

The peptoids provided herein may be used to make compositions capable of reversing or inhibiting RAGE expression both in vitro and in vivo and are capable of slowing or reversing the progression of RAGE-associated diseases or disorders in subjects suffering therefrom. In the methods, compositions comprising the peptoids described herein are administered to the subject in need of treatment. Suitably, the compositions are formulated and administered such that the peptoids are able to cross the blood-brain barrier. Suitably, the peptoids provided herein are able to treat or slow the progression of Alzheimer's disease, arthritis, rheumatoid arthritis, Takayasu's arthritis, atherosclerosis, congestive heart failure, myocardial infarction, peripheral vascular disease, diabetic neuropathy, diabetic nephropathy, diabetic retinopathy, psoriasis, Parkinson's disease, multiple sclerosis, amyotrophic lateral sclerosis, or Creutzfeldt-Jakob disease. Suitably, the subjects are mammals, more suitably, humans. Treatment of Alzheimer's disease includes, but is not limited to, prophylaxis of symptoms or indicators of the condition, reduction in disease severity or progression, or reversal, reduction, or slowing in disease progression as compared to an untreated subject.

The compositions described herein may be used to treat subjects in need of treatment for a RAGE-associated disease or disorder and may be used in combination with a second composition capable of inhibiting or slowing the progression of RAGE-associated disease or disorder. The two compositions used together to treat a subject may be administered simultaneously or concomitantly or one before the other in any order. The two compositions may be administered such that one is administered before the other with a difference in administration time of 1 hour, 2 hours, 4 hours, 8 hours, 12 hours, 16 hours, 20 hours, 1 day, 2 days, 4 days, 7 days, 2 weeks, 4 weeks, or more.

The compositions described herein may be administered by any means known to those skilled in the art, including, but not limited to, oral, topical, intranasal, intraperitoneal, parenteral, intravenous, intramuscular, subcutaneous, intrathecal, transcutaneous, nasopharyngeal, or via transmucosal absorption. Thus, the compositions may be formulated as an ingestible, injectable, intranasal, topical, or suppository formulation. The compositions may also be delivered within a liposomal or time-release vehicle. Suitably, the compositions are administered such that they are delivered or are able to cross the blood-brain barrier. Administration of the compositions to a subject appears to exhibit beneficial effects in a dose-dependent manner. Thus, within broad limits, administration of larger quantities of the compositions is expected to achieve increased beneficial biological effects than administration of a smaller amount. Moreover, efficacy is also contemplated at dosages below the level at which toxicity is seen.

It will be appreciated that the specific dosage administered in any given case will be adjusted in accordance with the composition or compositions being administered, the disease to be treated or inhibited, the condition of the subject, and other relevant medical factors that may modify the activity of the composition or the response of the subject, as is well known by those skilled in the art. For example, the specific dose for a particular subject depends on age, body weight, general state of health, diet, the timing and mode of administration, the rate of excretion, medicaments used in combination, and the severity of the particular disorder to which the therapy is applied. Dosages for a given patient can be determined using conventional considerations, e.g., by customary comparison of the differential activities of the composition of the invention and of a known agent, such as by means of an appropriate conventional pharmacological or prophylactic protocol.

The maximal dosage for a subject is the highest dosage that does not cause undesirable or intolerable side effects. The number of variables in regard to an individual prophylactic or treatment regimen is large, and a considerable range of doses is expected. The route of administration will also impact the dosage requirements. It is anticipated that dosages of the composition will inhibit progression of the condition by at least 10%, 20%, 30%, 40%, 50%, 60%, 70%, 80%, 90%, or 100% compared to pre-treatment symptoms or progression of the disease if left untreated. It is specifically contemplated that pharmaceutical preparations and compositions may palliate or alleviate symptoms of the disease without providing a cure, or, in some embodiments, may be used to stop progression of the disease or disorder and in some cases may even reverse progression.

Suitable effective dosage amounts for administering the compositions may be determined by those of skill in the art, but typically range from about 1 microgram to about 100,000 micrograms per kilogram of body weight weekly, although they are typically about 1,000 micrograms or less per kilogram of body weight weekly. In some embodiments, the effective dosage amount ranges from about 10 to about 10,000 micrograms per kilogram of body weight weekly. In another embodiment, the effective dosage amount ranges from about 50 to about 5,000 micrograms per kilogram of body weight weekly. In another embodiment, the effective dosage amount ranges from about 75 to about 1,000 micrograms per kilogram of body weight weekly. The effective dosage amounts described herein refer to total amounts administered, that is, if more than one composition is administered, the effective dosage amounts correspond to the total amount administered. The composition can be administered as a single dose or as divided doses. For example, the composition may be administered two or more times separated by 4 hours, 6 hours, 8 hours, 12 hours, a day, two days, three days, four days, one week, two weeks, or by three or more weeks.

An effective amount or a therapeutically effective amount as used herein means the amount of a composition that, when administered to a subject for treating a state, the disorder or condition is sufficient to affect a treatment (as defined above). The therapeutically effective amount will vary depending on the composition, formulation or composition, the disease and its severity, and the age, weight, physical condition, and responsiveness of the subject to be treated.

The present disclosure is not limited to the specific details of construction, arrangement of components, or method steps set forth herein. The compositions and methods disclosed herein are capable of being made, practiced, used, carried out, and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents form part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

Examples

JPT1a Prevents the Upregulation of RAGE and Modulates the Associated Inflammatory Response Upregulation of RAGE and modulation of inflammatory response was evaluated as shown in FIG. 1. THP-1 monocytes were differentiated into macrophages through exposure to phorbol 12-myristate 13-acetate (PMA) for three days prior to experimentation 10. THP-1 monocytes differentiated in this manner have been shown to closely resemble the behavior and phenotype of primary human monocyte-derived macrophages. Upon differentiation, these cells were then incubated (3 days) with media containing JPT1a (50, 10, or 2 µM) alone or JPT1a (50, 10, or 2 µM) in the presence of low-dose (2 ng/mL) lipopolysaccharide (LPS) as a chronic pro-inflammatory stimulus 11. Treatment with 2 ng/mL LPS alone served as a positive control, while treatment with an equivalent volume of buffer diluted into media served as the vehicle. Cellular supernatant was harvested on day 3 12; these samples were immediately centrifuged at 1200 rpm for 10 min at 25° C. to remove any cells or debris. The top 80% of this volume was subsequently removed and stored at −80° C. for later assessment of cytokines via ELISA. Cells were fixed and stained for RAGE, phalloidin (cytoplasmic marker), and DAPI (nuclear marker) 13. Each channel was imaged with a Zeiss LSM 510 META Confocal Scanning Laser Microscope using a plan-neofluar 40×/1.3 oil DIC immersion objective; three of these multi-channel images were obtained from each slide in each experiment 14. All multi-channel images were converted to TIFF file format via ImageJ64 software for quantitative image analysis using a custom subroutine written in Matlab™ software to obtain the average RAGE expression per volume of cells, and the data generated was assessed for statistical significance using GraphPad Prism 7.0 software 15.

Figure 2A:
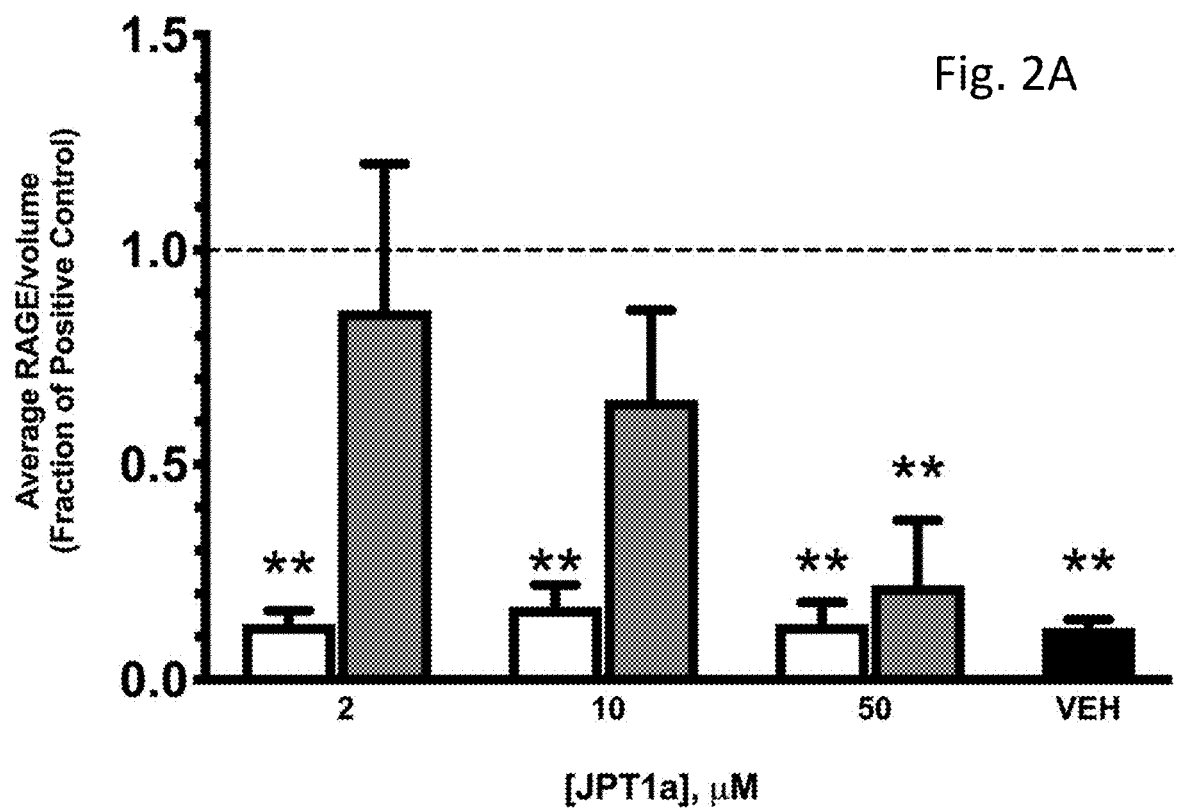
FIG. 2A shows that JPT1a modulates transmembrane RAGE expression in a dose-dependent manner.

As shown in FIG. 2A, THP-1 macrophages were treated with JPT1a alone (white) or in the presence of a chronic low-dose (2 ng/mL) of LPS (as a pro-inflammatory stimulus) (grey) for 3 days prior to fixation and staining for RAGE. Images acquired via confocal microscopy were analyzed via custom MATLAB™ subroutine to determine the average quantity of RAGE present within a given volume of cells. Results within each experiment are normalized to the positive control (2 ng/mL LPS alone), indicated by the dashed line at 1. Significance relative to positive control is indicated as ** $p<0.01$. Error bars indicate SEM, n=4. These results indicate that the upregulation in RAGE expression observed in the presence of the pro-inflammatory stimulus (LPS) is reduced in a dose-dependent and significant manner when cells are simultaneously exposed to JPT1a. In addition, treatment with JPT1a alone does not provoke significant response or upregulation in the expression of RAGE relative to the control.

Figure 2B:
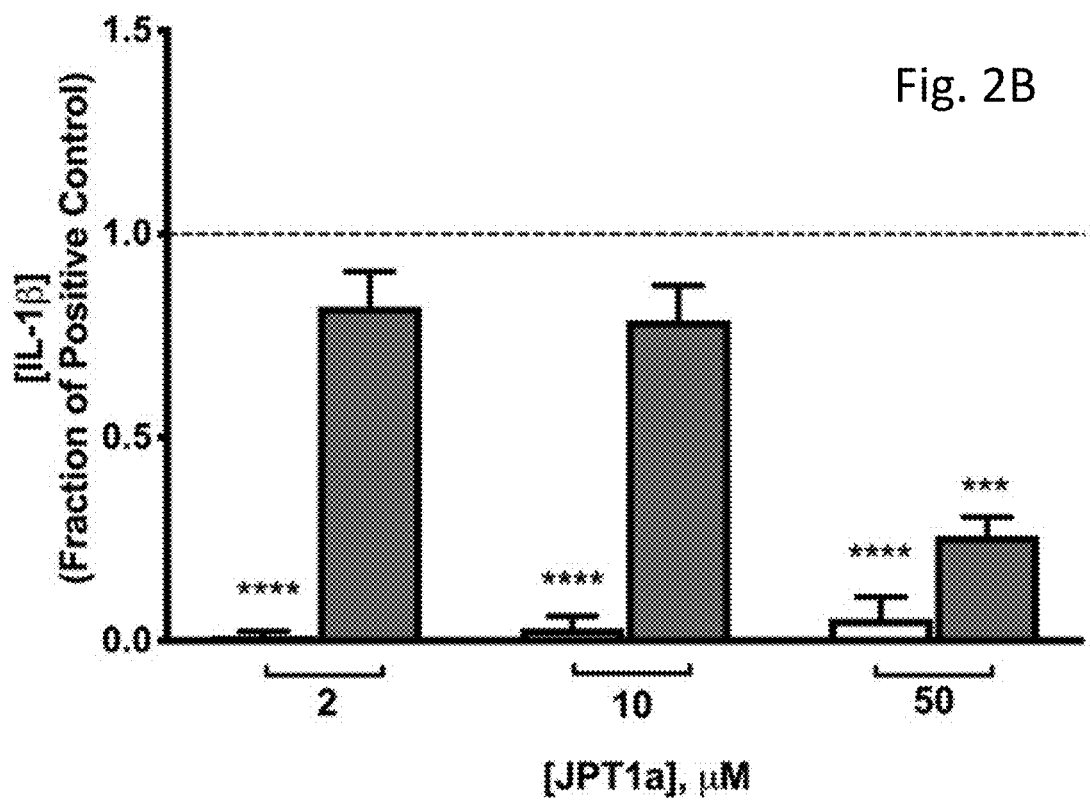
FIGS. 2B-2D show that JPT1a attenuates pro-inflammatory cytokine expression of IL-1β (FIG. 2B), IL-6 (FIG. 2C), and IL-8 (FIG. 2D).
Figure 2C:
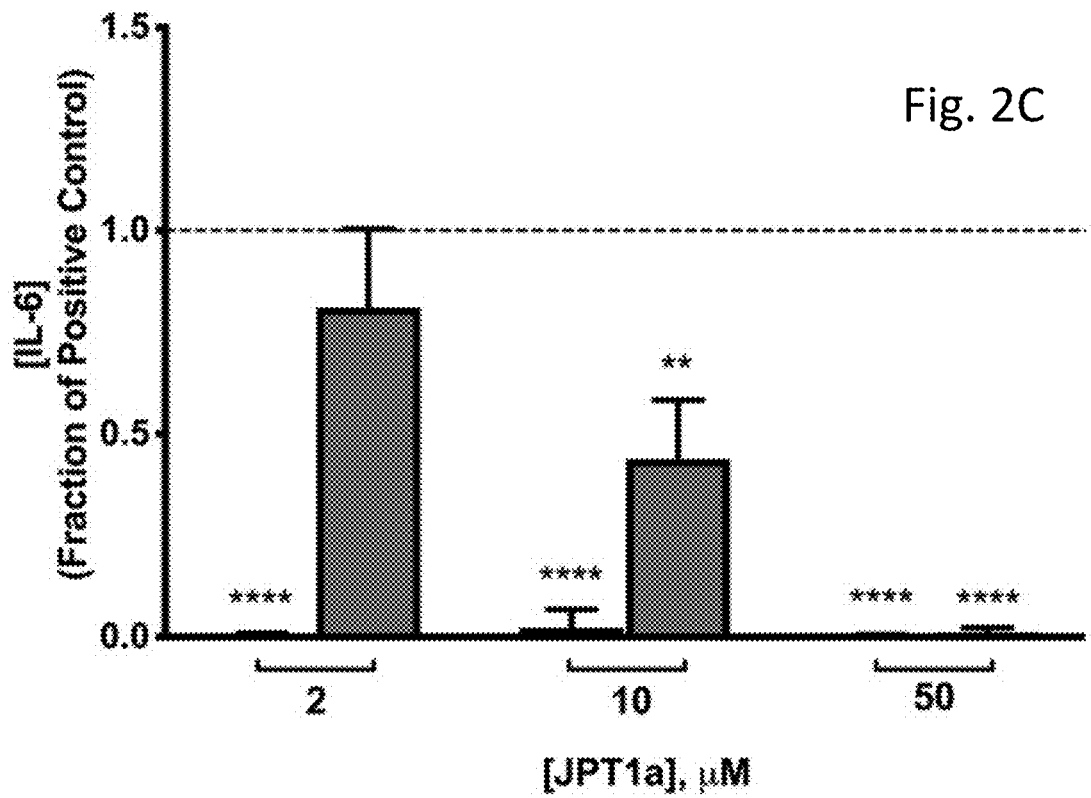
Figure 2D:
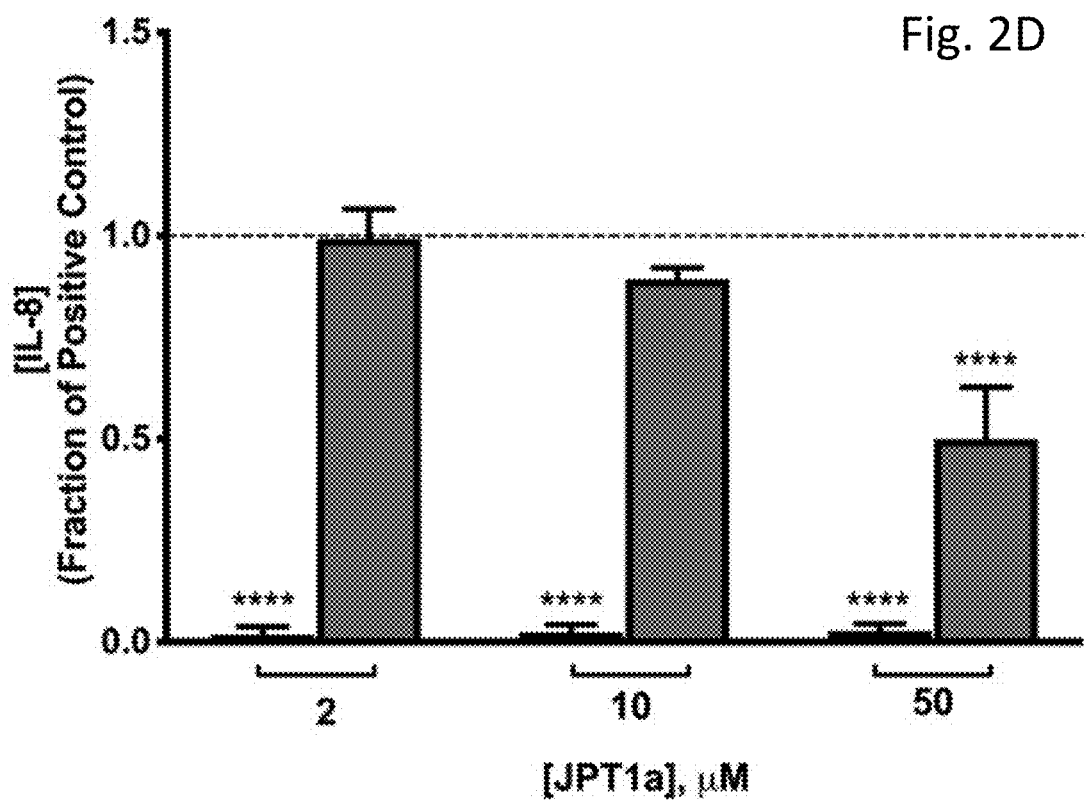

As shown in FIGS. 2B-2D, THP-1 macrophages were treated with JPT1a alone (white) or in the presence of a chronic low-dose (2 ng/mL) of LPS (grey), for 3 days prior to supernatant harvest and storage. Examination of the supernatant via ELISA determined the concentrations of (FIG. 2B) IL-1β, (FIG. 2C) IL-6, and (FIG. 2D) IL-8. Results are reported as a fraction of the positive control (2 ng/mL LPS alone) indicated by the dashed line at 1.0.  $p<0.01$, * $p<0.001$, **** $p<0.0001$ vs positive control. Error bars indicate SEM, n=3-4. These results indicate that treatment with JPT1a at 50 µM significantly attenuates the LPS-induced production of cytokines IL-1β, IL-6, and IL-8; treatment with JPT1a at 10 µM also significantly reduces levels of LPS-induced IL-6 and IL-8.

JPT1a Reverses the Upregulation of RAGE

Reversal of RAGE and modulation of inflammatory response was evaluated as shown in FIG. 3. THP-1 monocytes were differentiated as described above 20. Upon differentiation, these cells were then incubated (48 h) with media containing low-dose (2 ng/mL) LPS as a chronic pro-inflammatory stimulus 21. Following incubation, JPT1a or JPT1 was added for final concentrations of 25, 5, and 1 µM 22, and cells were incubated an additional 24 h. Treatment with 2 ng/mL LPS alone served as a positive control, while treatment with an equivalent volume of buffer diluted into media served as the vehicle. Media was collected for later assessment of cytokines via ELISA as described above 23. Cells were fixed and stained for RAGE, phalloidin (cytoplasmic marker), and DAPI (nuclear marker) 24. Each channel was imaged with a Zeiss LSM 510 META Confocal Scanning Laser Microscope using a plan-neofluar 40×/1.3 oil DIC immersion objective; three of these multi-channel images were obtained from each slide in each experiment. 25 All multi-channel images were converted to TIFF file format via ImageJ64 software for quantitative image analysis using a custom subroutine written in Matlab™ software to obtain the average RAGE expression per volume of cells, and the data generated was assessed for statistical significance using GraphPad Prism 7.0 software 26.

Figure 4A:
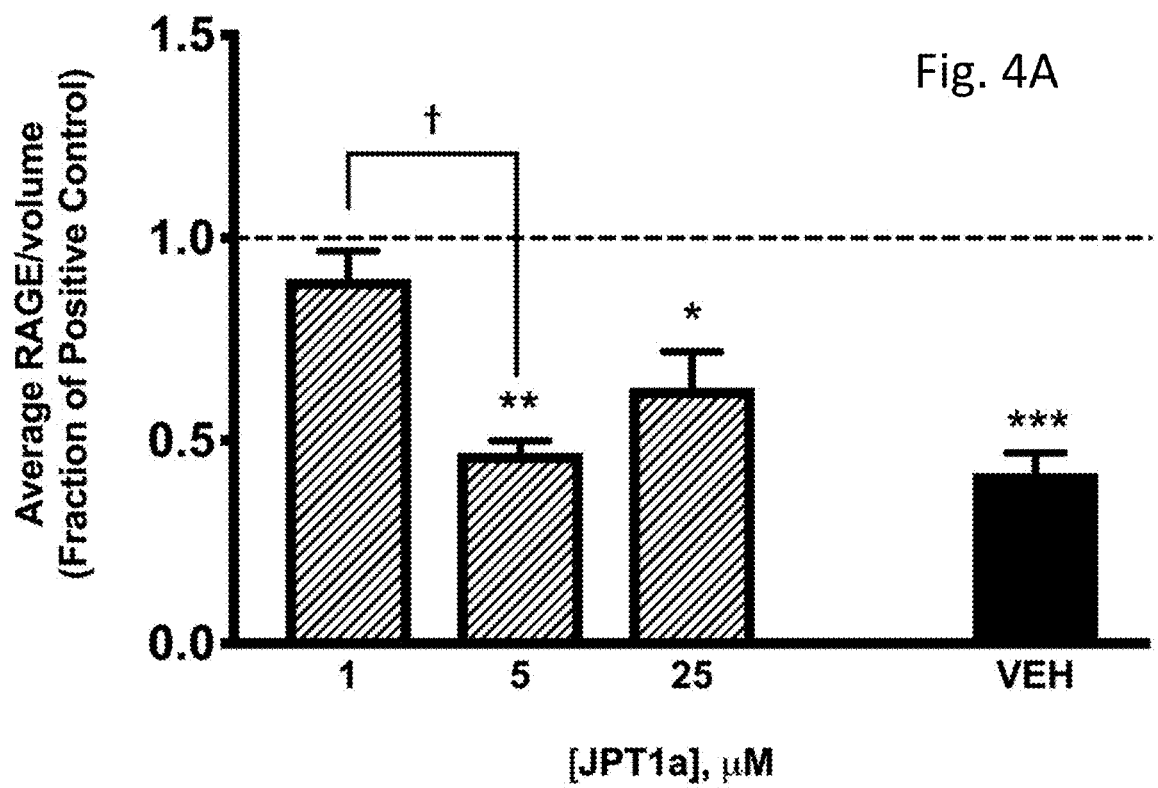
FIG. 4A shows that JPT1a reduces transmembrane RAGE expression in previously-stimulated macrophages.

As shown in FIG. 4A, THP1 macrophages were treated with low-dose LPS at 2 ng/mL. After 48 hours, half of the supernatant was removed, treated with JPT1a (dashed-grey) at final concentrations of 25, 5, 1, and 0 µM (positive control), and then added back to respective samples. Following an additional 24 h incubation, cells were fixed, stained, and imaged via confocal microscopy. Images were analyzed via custom MATLAB™ subroutine to determine the average quantity of RAGE present within a given volume of cells. Results within each experiment are normalized to the positive control (2 ng/mL LPS alone), indicated by the dashed line at 1.0. *p<0.05, **p<0.01 vs positive control. Significance between treatments indicated as †p<0.05. Error bars indicate SEM; n=4. These results demonstrate a significant reversal in LPS-induced RAGE expression in macrophages upon treatment at 25 and 5 µM JPT1a.

Figure 4B:
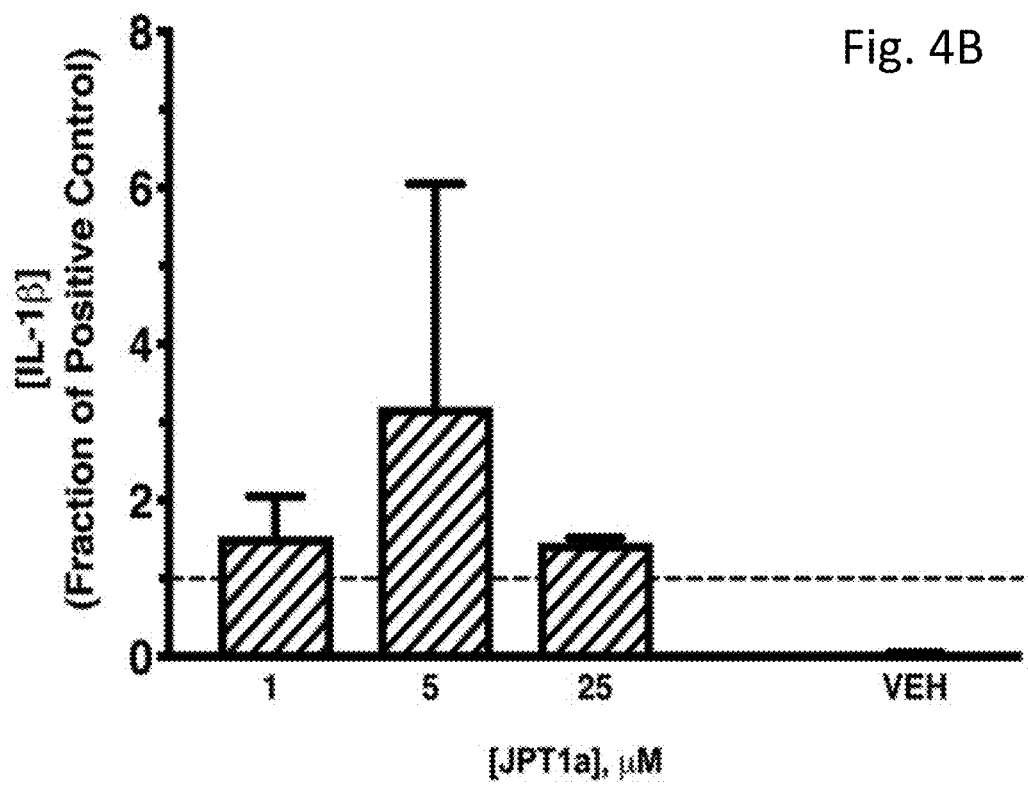
FIGS. 4B-4D show that JPT1a does not affect pro-inflammatory cytokine expression of IL-1β (FIG. 4B), IL-6 (FIG. 4C), and IL-8 (FIG. 4D) in previously stimulated macrophages.
Figure 4C:
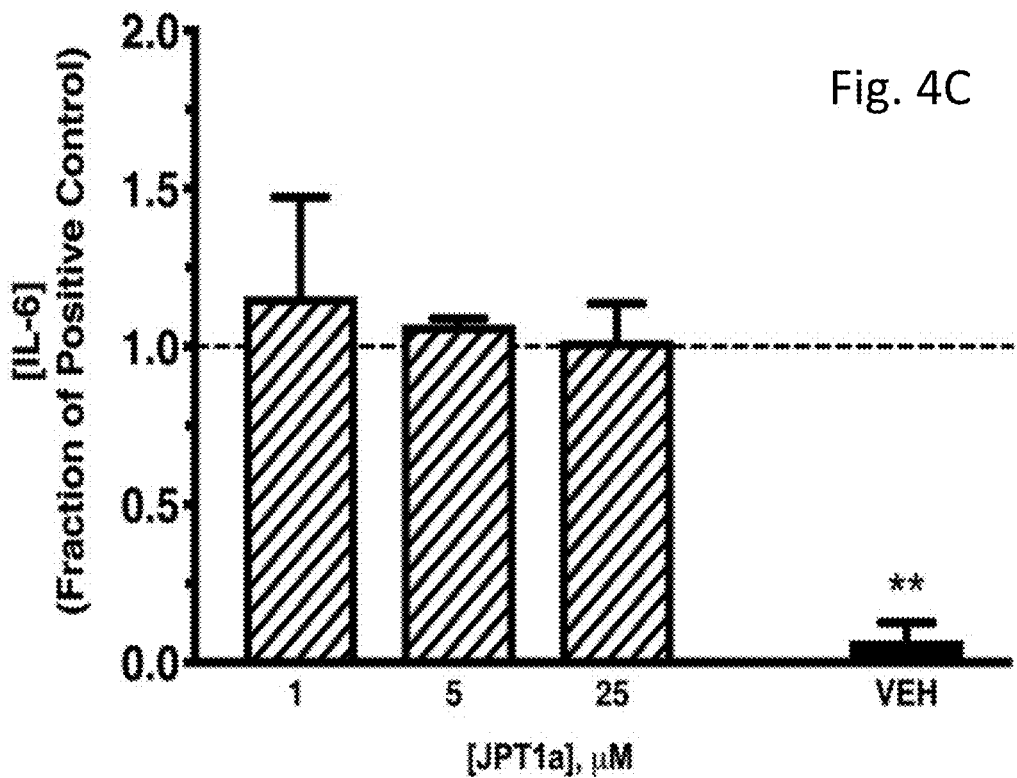
Figure 4D:
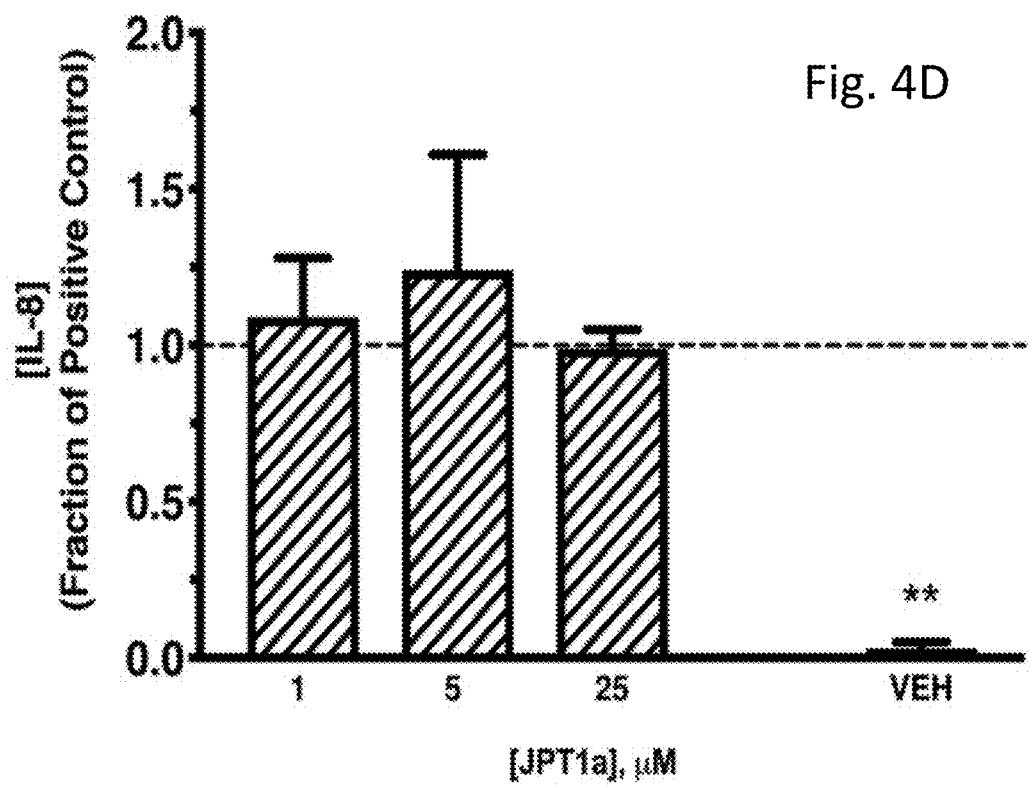

JPT1a does not Affect Inflammatory Cytokine Production in Previously Stimulated Macrophages As shown in FIGS. 4B-4D, THP1 macrophages were treated with low-dose LPS at 2 ng/mL. After 48 hours, half of the supernatant was removed, treated with JPT1a (dashed-grey) at final concentrations of 25, 5, 1, and 0 µM (positive control), and then added back to respective samples. Following an additional 24 h incubation, supernatant was harvested and examined for expression of IL-1β (FIG. 4B), IL-6 (FIG. 4C), and IL-8 (FIG. 4D) via ELISA. Results within each experiment are normalized to the positive control (2 ng/mL LPS alone), indicated by the dashed line at 1.0. *p<0.001, **p<0.0001 vs positive control. Error bars indicate SEM; n=2-3. These results indicate that JPT1a does not affect cytokine production of previously stimulated macrophages.

Figure 5A:
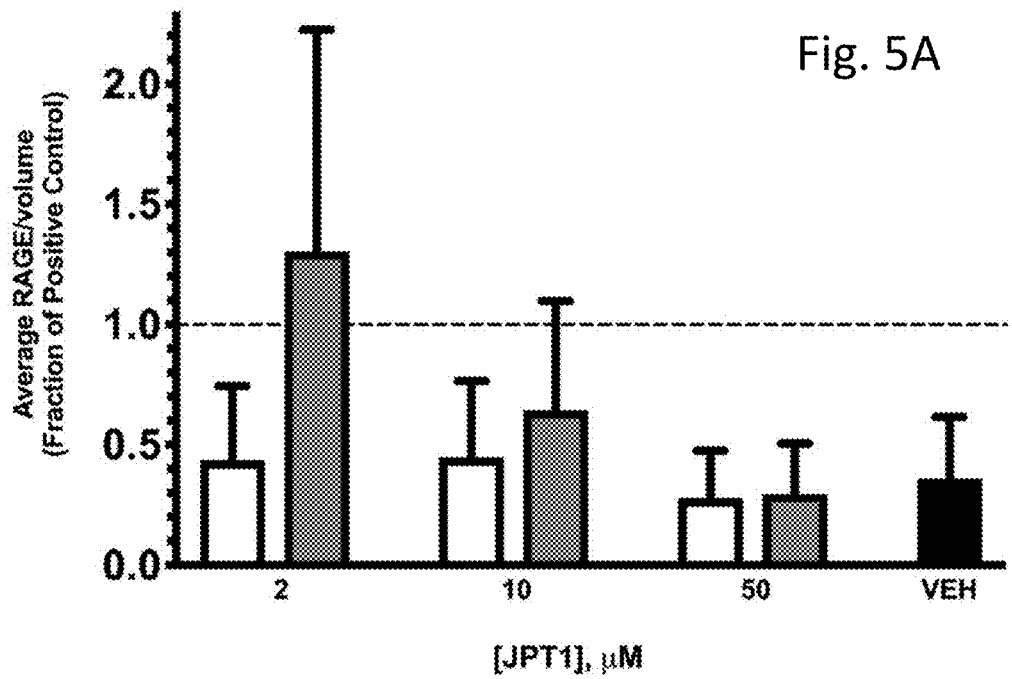
FIG. 5A shows that JPT1 modulates transmembrane RAGE expression in a dose-dependent manner.

JPT1 Prevents the Upregulation of RAGE and Modulates the Associated Inflammatory Response As shown in FIG. 5A, THP-1 macrophages were treated with JPT1 alone (white) or in the presence of a chronic low-dose (2 ng/mL) of LPS (grey), for 3 days prior to fixation and staining for RAGE as described above (FIG. 1). Images acquired via confocal microscopy were analyzed via custom MATLAB™ subroutine to determine the average quantity of RAGE present within a given volume of cells. Results within each experiment are normalized to the positive control (2 ng/mL LPS alone), indicated by the dashed line at 1.0. Error bars indicate SEM; n=2. These results indicate that the upregulation in RAGE expression observed in the presence of the pro-inflammatory stimulus (LPS) is reduced in a dose-dependent manner when cells are simultaneously exposed to JPT1. In addition, treatment with JPT1 alone does not provoke response or upregulation in the expression of RAGE relative to the control.

Figure 5B:
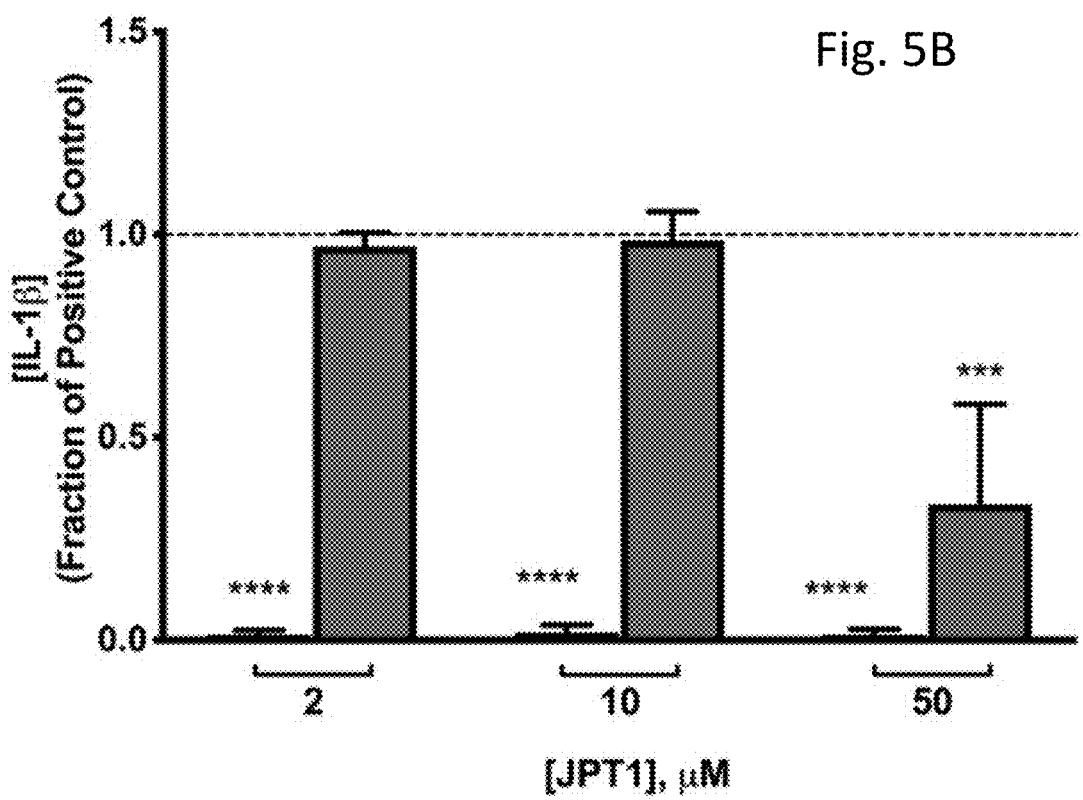

As shown in FIGS. 5B-5D, THP-1 macrophages were treated with JPT1 alone (white) or in the presence of a chronic low-dose (2 ng/mL) of LPS (grey), for 3 days prior to supernatant harvest and storage. Examination of the supernatant via ELISA determined the concentrations of (FIG. 5B) IL-1β, (FIG. 5C) IL-6, and (FIG. 5D) IL-8. Results within each experiment are normalized to the positive control (2 ng/mL LPS alone), indicated by the dashed line at 1. * p<0.05,  p<0.01, * p<0.001, **** p<0.0001 vs positive control. Error bars indicate SEM; n=2-4. These results indicate that treatment with JPT1 at 50 µM significantly attenuates the LPS-induced production of cytokines IL-1β and IL-6;

JPT1a is Non-Toxic to THP-1 Macrophages

Figure 6A:
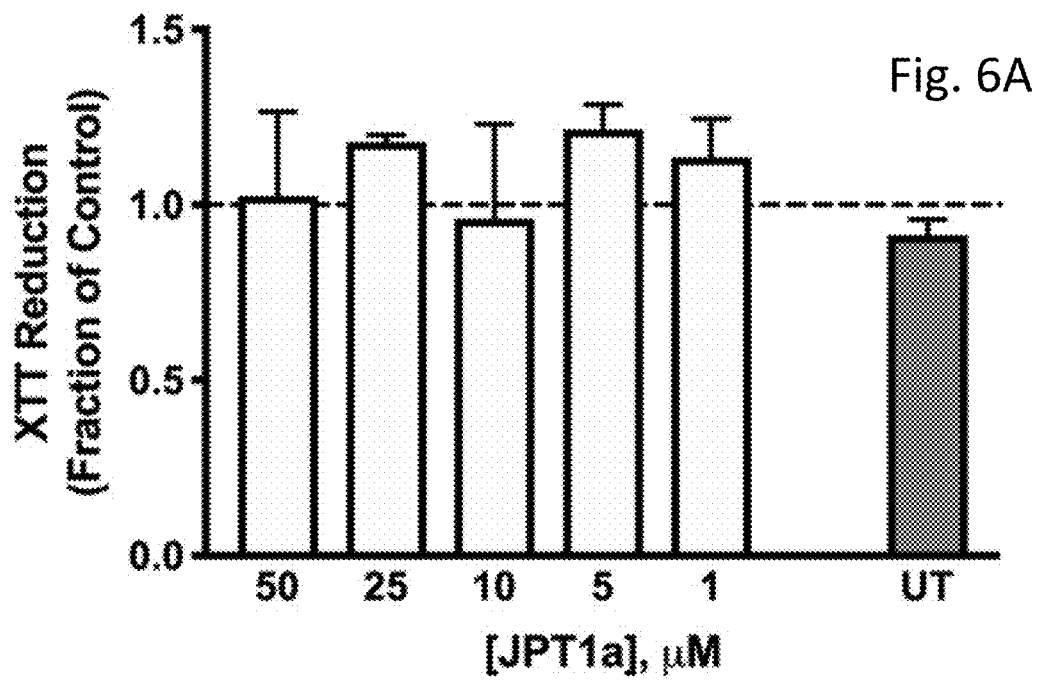
FIGS. 6A-6C show that JPT1a is non-toxic to THP-1 macrophages as evaluated via XTT assay at 2 h (FIG. 6A), 4 h (FIG. 6B), and 24 h (FIG. 6C).
Figure 6B:
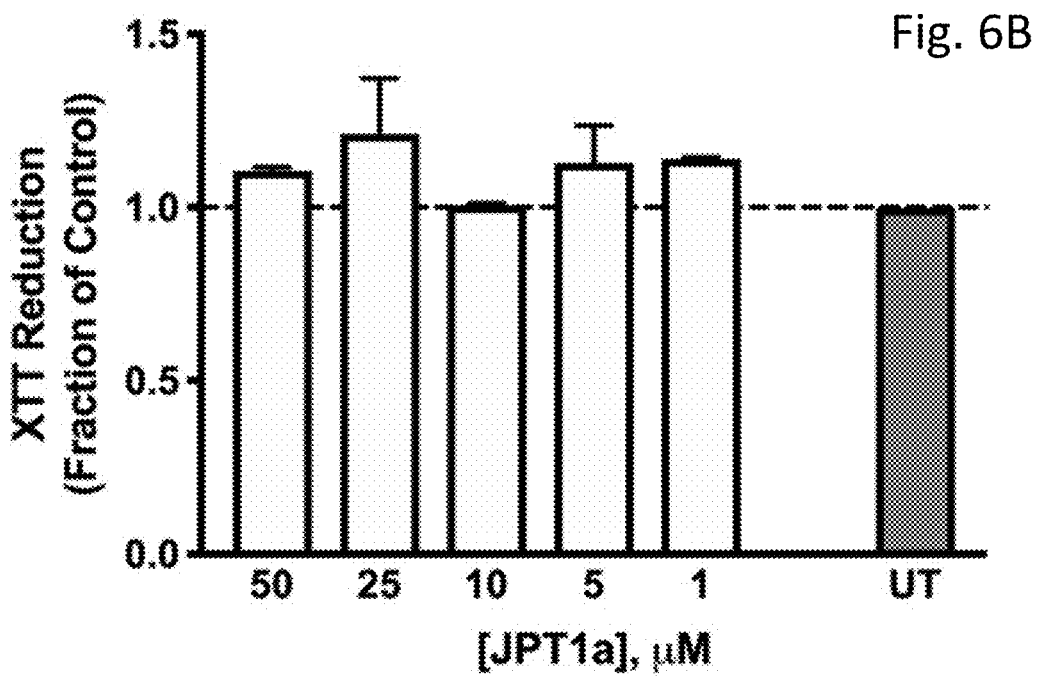
Figure 6C:
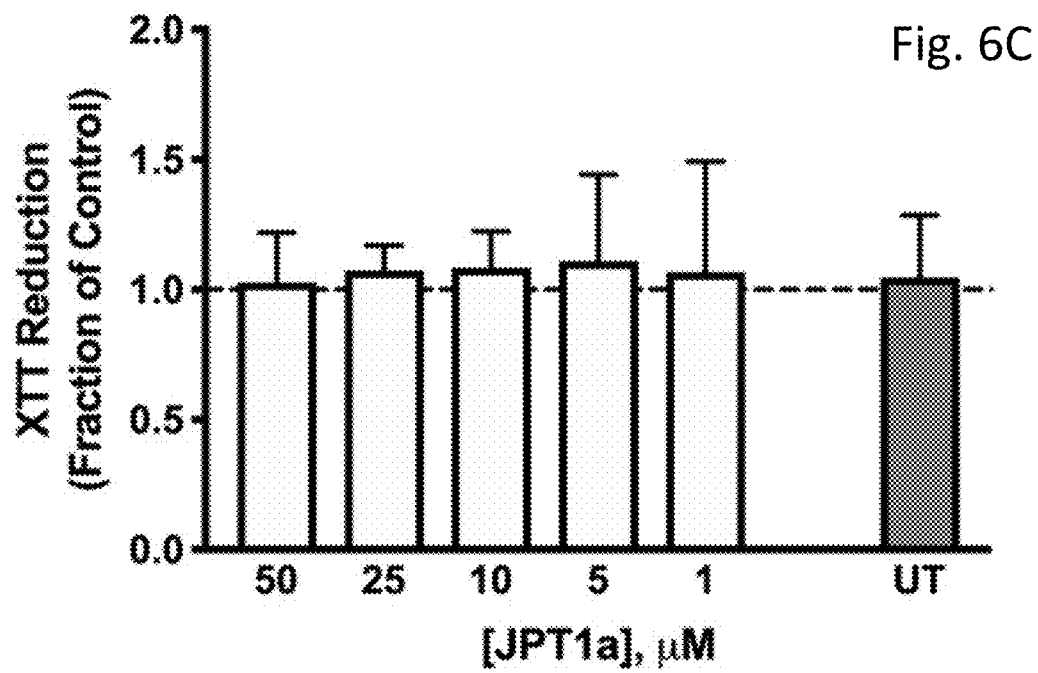

As shown in FIGS. 6A-6C, THP-1 macrophages remained untreated (grey) or were treated with JPT1a (white) at concentrations ranging from 1 to 50 µM. Toxicity was evaluated via XTT assay (Altman F P. Tetrazolium salts and formazans. Prog Histochem Cytochem. 1976; 9(3):1-56) at 2 h (FIG. 6A), 4 h (FIG. 6B), and 24 h (FIG. 6C) and it was determined that no change occurred in cells treated with JPT1a relative to cells treated with the vehicle alone. Results are reported as a fraction of cells treated with the vehicle alone, as indicated by the dashed line at 1. Error bars indicate SEM; n=2. These results indicate that JPT1a was non-toxic to macrophages even up to concentrations of 50 µM.

JPT1a and JPT1 Bind to RAGE Selectively

Figure 7A:
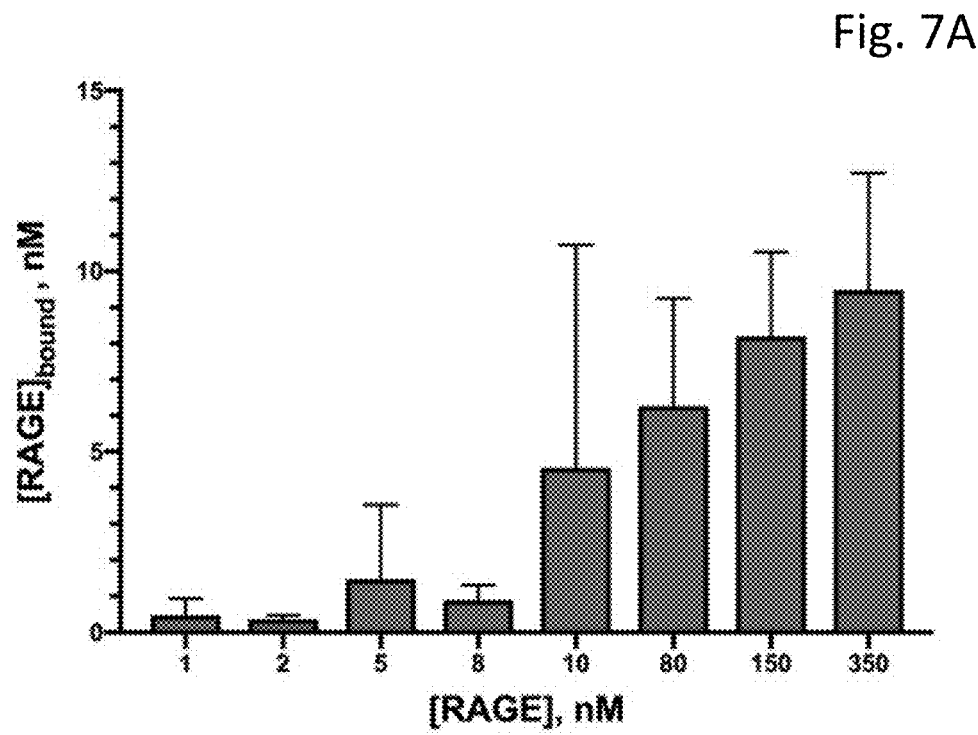
FIGS. 7A-7D show that JPT1a and JPT1 bind to RAGE selectively and with high affinity.
Figure 7B:
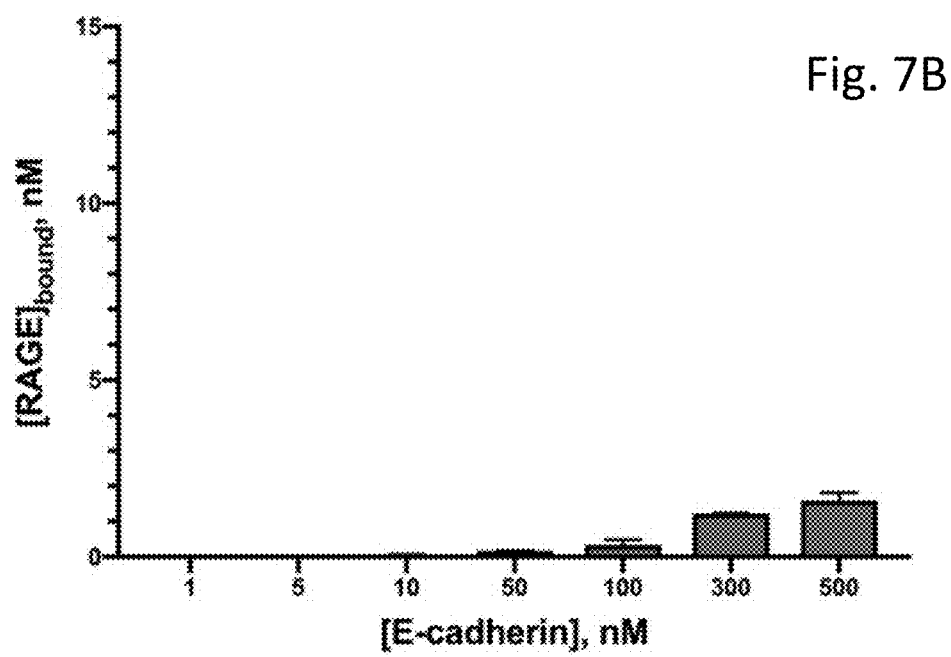
Figure 7C:
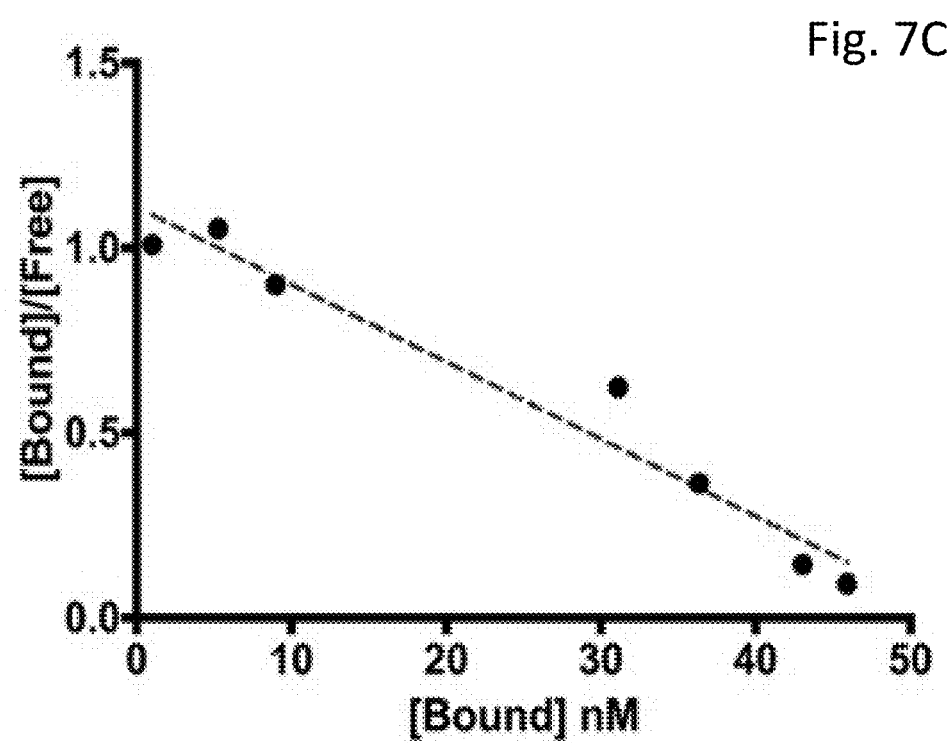
Figure 7D:
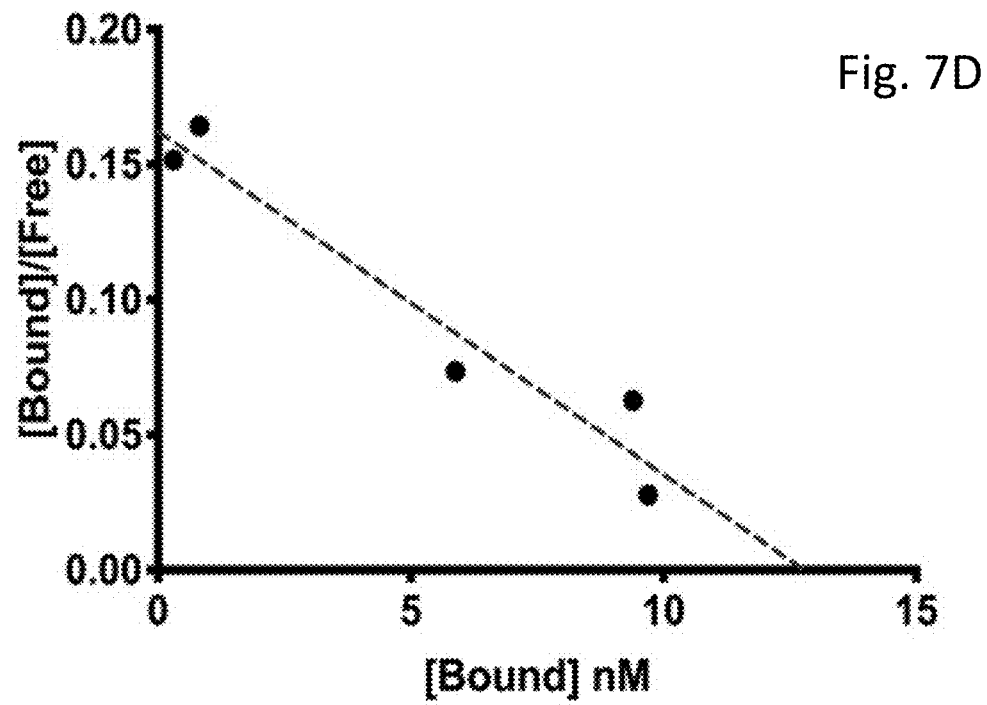

As shown in FIGS. 7A-7D, 96-well plates coated with 500 nM JPT1a were treated with concentrations of RAGE (FIG. 7A) or E-cadherin (FIG. 7B) ranging from 1 to 500 nM. Values are reported as the average concentration of bound protein determined from all experiments. Error bars indicate SEM, n=2-5. FIG. 7C shows a Scatchard plot for RAGE binding, which represents data generated from one trial; an average $K_d$=51.8±7.3 nM was calculated from n=3. In FIG. 7D, 96-well plates coated with 500 nM JPT1 were treated with concentrations of RAGE ranging from 1 to 350 nM. This Scatchard plot for RAGE binding represents data generated from one trial that produced a $K_d$=78.8 nM, n=1. The concentrations of bound JPT1a-RAGE, shown in FIG. 7A, demonstrate a clear relationship of dose-dependence. In contrast, an absence of binding between JPT1a and E-cadherin, a cell adhesion molecule ubiquitously expressed on macrophages, is observed in FIG. 7B. The distinct difference in the binding relationships between the peptoid and these two molecules demonstrates the selectivity of these peptoids for RAGE. Furthermore, the binding between RAGE and both JPT1a and JPT1 is of high affinity, demonstrated by the nanomolar $K_d$ values obtained from Scatchard plots in FIGS. 7C and 7D for this assay format.

JPT1a Binds to RAGE with Low Nanomolar Affinity

Figure 8A:
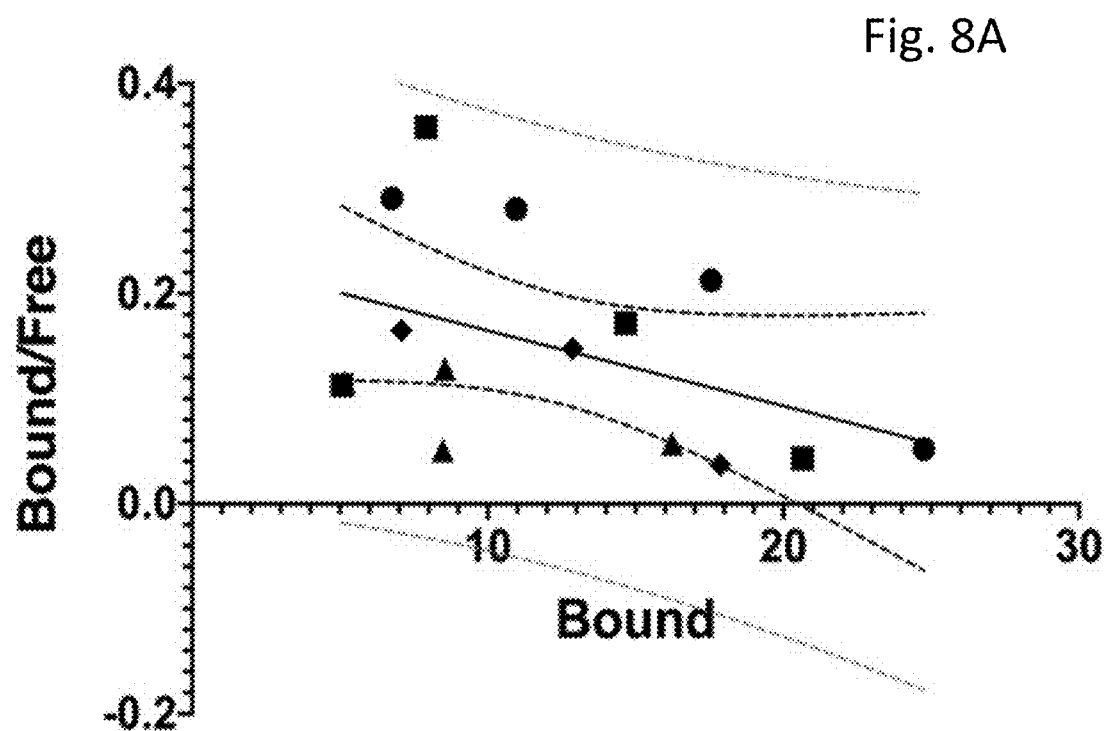
FIGS. 8A-8B show that JPT1a binds to RAGE with low nanomolar affinity.
Figure 8B:
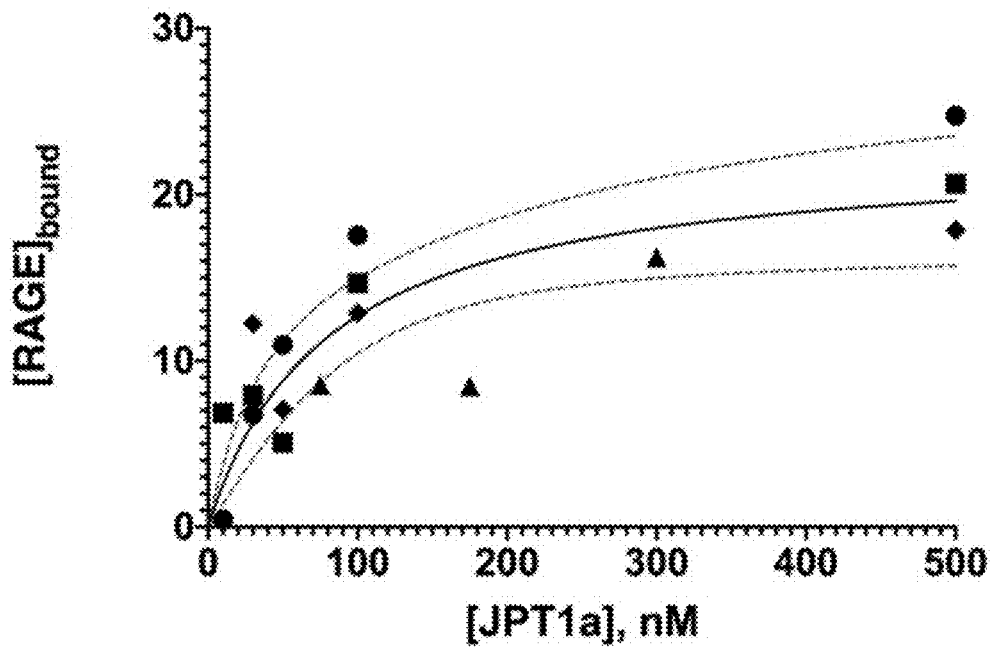

Definitive binding affinity of JPT1a for RAGE was determined from binding equilibrium attained in solution. As shown in FIGS. 8A-8B, 96-well plates coated with 500 nM JPT1a were treated with overnight incubations containing 20 nM RAGE and JPT1a in concentrations ranging from 0 nM to 1000 nM. Absorbance values were used to calculate relative [RAGE]$_{bound}$ and [RAGE]$_{free}$ via the Cheng-Prussoff method (Friguet B, Chaffotte A F, Djavadi-Ohaniance L, Goldberg M E. Measurements of the true affinity constant in solution of antigen-antibody complexes by enzyme-linked immunosorbent assay. J Immunol Methods. 1985; 77(2): 305-319; Rath S, Stanley C M. An inhibition enzyme immunoassay for estimating relative antibody affinity and affinity heterogeneity. 1988; 106:245-249; Newton P, Harrison P, Clulow S. A Novel Method for Determination of the Affinity of Protein: Protein Interactions in Homogeneous Assays. 2008:674-682). FIG. 8A. Experimental values from four separate experiments (distinguished by circles, squares, diamonds, and triangles) were plotted via Scatchard plot, which estimates a binding affinity of JPT1a for RAGE of 139.5 nM. Black dashed lines indicate 95% confidence interval, and gray dashed lines indicate 95% prediction interval, n=4. FIG. 8B. Data was also analyzed via plot of specific binding (one epitope) to yield $K_d$ of 79.0±28.4 nM. Dashed lines indicate 95% confidence interval, n=3. These experiments report a low nanomolar binding affinity of JPT1a for RAGE, demonstrating a high binding affinity that is within the range of other drug-like molecules.

JPT1a Reduces RAGE Upregulation in the Presence of Pre-Formed Aβ Oligomers.

Aβ$_{1-42}$ oligomers were prepared at 15 μM through the addition of 12 mM phosphate containing 5 μM NaCl to DMSO-solubilized AP. After 15-minute incubation, oligomerization was halted and used to immediately prepare treatments of 10 nM Aβ$_{1-42}$ oligomers alone (positive control) or in the presence of the peptoid at concentrations ranging from 1 μM to 25 μM. Treatments were applied to THP1 macrophages for 3 days prior to cell fixation and staining. Treatment with 10 nM Aβ$_{1-42}$ oligomers alone served as a positive control, while treatment with an equivalent volume of buffer diluted into media served as the vehicle. Treatment with 15 μM JPT1a ensured that JPT1a alone had no effect. Cells were fixed and stained for RAGE, phalloidin (cytoplasmic marker), and DAPI (nuclear marker). Each channel was imaged with a Zeiss LSM 510 META Confocal Scanning Laser Microscope using a plan-neofluar 40×/1.3 oil DIC immersion objective; three of these multi-channel images were obtained from each slide in each experiment. All multi-channel images were converted to TIFF file format via ImageJ64 software for quantitative image analysis using a custom subroutine written in MATLAB™ software to obtain the average RAGE expression per volume of cells.

Figure 9:
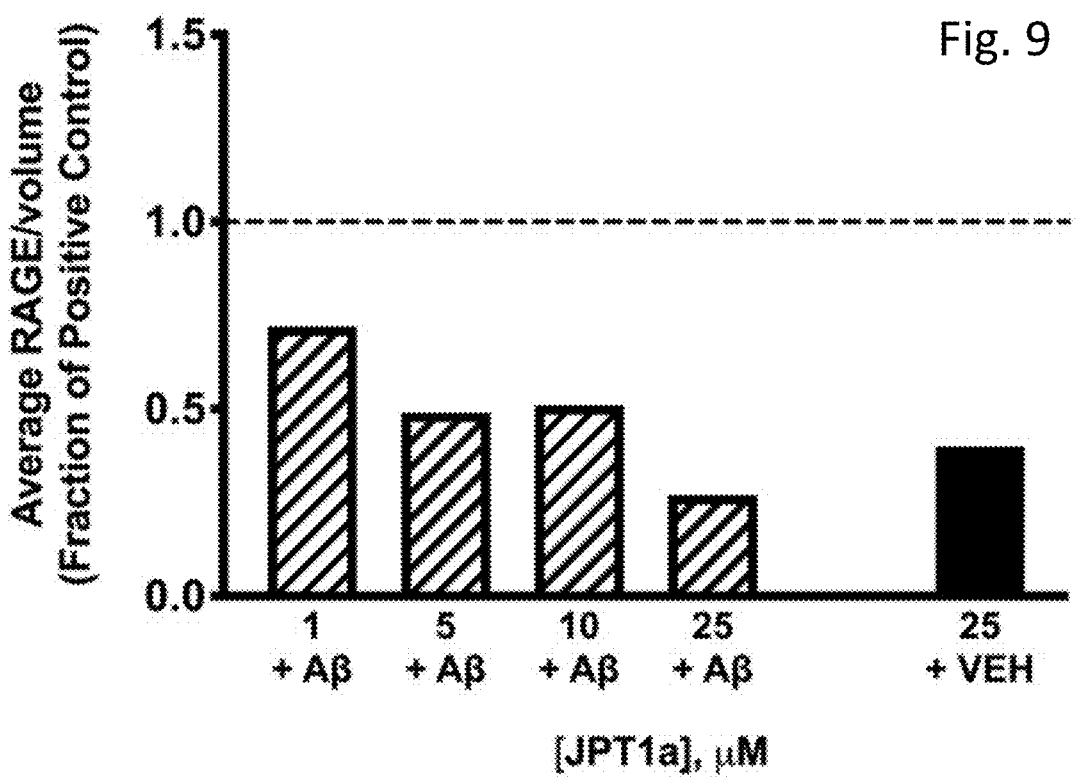

As shown in FIG. 9, THP1 macrophages were treated with 10 nM Aβ$_{1-42}$ oligomers alone (positive control) or in the presence of JPT1a (25, 10, 5, or 1 μM) (dashed). Treatment with an equivalent volume of buffer diluted into media served as the vehicle. Treatment with 25 μM JPT1a in the presence of vehicle assessed the effect of the peptoid alone (black). Images were analyzed via custom MATLAB™ subroutine to determine the average quantity of RAGE present within a given volume of cells. Data shown represent the average of a single experiment containing 3 replicates, with all results reported as a fraction of the positive control, indicated by the dashed line at 1.0. These results indicate a dose-dependent reduction in Aβ$_{1-42}$ oligomer induced RAGE expression in macrophages upon treatment with JPT1a. In addition, treatment with JPT1a alone does not provoke significant response or upregulation in the expression of RAGE.

We claim:

1. A method for reversing or inhibiting receptor for advanced glycation end products (RAGE) expression in a cell presented with a stimulator of an innate immune response, the method comprising contacting the cell presented with the stimulator of the innate immune response with an effective amount of a peptoid comprising a segment of formula

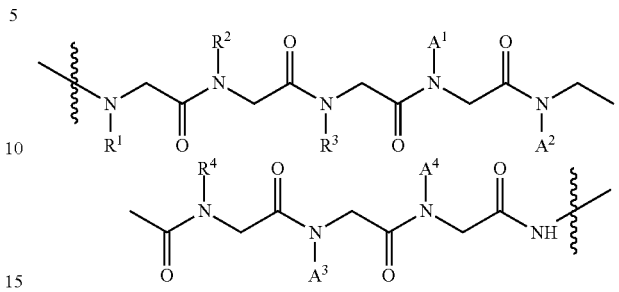

to reverse or inhibit RAGE expression in the cell,
wherein $R^1$, $R^2$, $R^3$, and $R^4$ are independently selected from a branched or an unbranched, saturated or unsaturated, substituted or unsubstituted $C_1$-$C_{10}$ alkyl group, and $A^1$, $A^2$, $A^3$, and $A^4$ are independently selected from a branched or an unbranched, substituted or unsubstituted $C_6$-$C_{12}$ aryl or $C_6$-$C_{12}$ arylalkyl group.

2. The method of claim 1, wherein the effective amount of the peptoid to reverse or inhibit RAGE expression in the cell is an effective amount of the peptoid to reverse or inhibit accumulation of a cytokine in the cell or production of a cytokine by the cell.

3. The method of claim 2, wherein the cytokine comprises IL-1β, IL-6, IL-8, or a combination thereof.

4. The method of claim 1, wherein the stimulator of the innate immune response is a damage-associated molecular pattern (DAMP) or a pathogen-associated molecular pattern molecules (PAMP).

5. The method of claim 4, wherein the stimulator of the innate immune response comprises a molecule selected from the group consisting of an advanced glycation end-product (AGE), amyloid-β (Aβ), HMGB1, a S100, a nucleic acid, a bacterial endotoxin, and a virus.

6. The method of claim 5, wherein the stimulator of the innate immune response comprises Aβ.

7. The method of claim 1, wherein the peptoid comprises a longer peptoid chain than the segment.

8. The method of claim 1, wherein the peptoid comprises

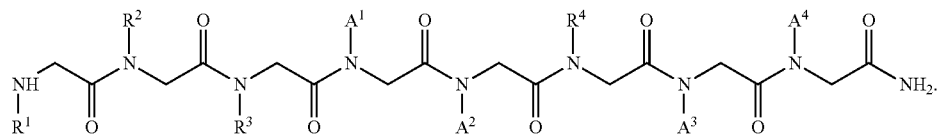

with all results reported as a fraction of the positive control, indicated by the dashed line at 1.0. These results indicate a 9. The method of claim 1, wherein $R^1$ comprises a terminally substituted $C_1$-$C_6$ aminoalkyl group.

10. The method of claim 1, wherein $R^1$ comprises 4-butylamine.

11. The method of claim 1, wherein $R^2$, $R^3$, and $R^4$ are independently selected from a branched or an unbranched, saturated or unsaturated, substituted or unsubstituted $C_1$-$C_6$ alkyl group.

12. The method of claim 11, wherein each of $R^2$, $R^3$, and $R^4$ comprise the same group.

13. The method of claim 11, wherein each of $R^2$, $R^3$, and $R^4$ comprise a propyl group or each of $R^2$, $R^3$, and $R^4$ comprise a 1-methyl-prop-1-yl group.

14. The method of claim 1, wherein each of $A^1$, $A^2$, $A^3$, and $A^4$ are independently selected from a branched or an unbranched, substituted or unsubstituted $C_6$ aryl or $C_7$-$C_8$ arylalkyl group.

15. The method of claim 14, wherein each of $A^1$, $A^2$, $A^3$, and $A^4$ comprise the same group.

16. The method of claim 14, wherein each of $A^1$, $A^2$, $A^3$, and $A^4$ comprise benzyl or each of $A^1$, $A^2$, $A^3$, and $A^4$ comprise 1-phenylethyl.

17. The method of claim 1, wherein the peptoid is JPT1a or JPT1.

\* \* \* \* \*